US007622248B2

(12) United States Patent
Suga et al.

(10) Patent No.: US 7,622,248 B2
(45) Date of Patent: Nov. 24, 2009

(54) RIBOZYMES WITH BROAD TRNA AMINOACYLATION ACTIVITY

(75) Inventors: Hiroaki Suga, Williamsville, NY (US); Hiroshi Murakami, Amherst, NY (US); Hirohide Saito, Tokyo (JP)

(73) Assignee: The Research Foundation of State University of New York, Buffalo, NY (US)

( * ) Notice: Subject to any disclaimer, the term of this patent is extended or adjusted under 35 U.S.C. 154(b) by 311 days.

(21) Appl. No.: 10/369,036

(22) Filed: Feb. 18, 2003

(65) Prior Publication Data

US 2003/0228593 A1 Dec. 11, 2003

Related U.S. Application Data

(60) Provisional application No. 60/357,424, filed on Feb. 15, 2002.

(51) Int. Cl.
*C12Q 1/68* (2006.01)
*C12P 19/34* (2006.01)
*C07H 21/00* (2006.01)
*C07H 21/02* (2006.01)
*C07H 21/04* (2006.01)

(52) U.S. Cl. ............... 435/6; 435/91.31; 536/22.1; 536/23.1; 536/23.2

(58) Field of Classification Search ............... None
See application file for complete search history.

(56) References Cited

U.S. PATENT DOCUMENTS

| 5,270,163 | A |  | 12/1993 | Gold et al. |  |
| 5,475,096 | A |  | 12/1995 | Gold et al. |  |
| 5,871,924 | A | * | 2/1999 | Yarus et al. | ............ 435/6 |
| 5,990,142 | A |  | 11/1999 | Carganico et al. |  |
| 5,998,142 | A |  | 12/1999 | Gold et al. |  |
| 6,063,566 | A |  | 5/2000 | Joyce |  |
| 6,280,936 | B1 | * | 8/2001 | Burgin et al. | ............ 435/6 |

FOREIGN PATENT DOCUMENTS

| WO | WO 9936517 A2 * | 7/1999 |
| WO | WO 01/38582 A1 | 5/2001 |
| WO | WO 0138582 A1 * | 5/2001 |

OTHER PUBLICATIONS

Behrens et al. Tetrahedron, 2000, vol. 56, pp. 9443-9449.*
Ma et al. Biochemistry, 1993, vol. 32, pp. 7939-7945.*
Lee et al. Nature Structural Biology, vol. 7, No. 1, pp. 28-33, Jan. 2000.*
Derwent Summary of WO9936517A2 in English.*
Bartel, David P. et al., "Isolation Of New Ribozymes From A Large Pool Of Random Sequences," *Science*, Sep. 10, 1993, pp. 1411-1418, vol. 261, No. 5127.
Beaudry, Amber A. et al., "Directed Evolution Of An RNA Enzyme," *Science*, Jul. 31, 1992, pp. 635-641, vol. 257, No. 5070.

Brenner, Sydney et al., "Encoded Combinatorial Chemistry," *Proc. Natl. Acad. Sci. USA*, Jun. 1992, pp. 5381-5383, vol. 89.
Fechter, Pierre et al., "Ribozyme Processed tRNA Transcripts With Unfriendly Internal Promoter For T7 RNA Polymerase: Production And Activity," *FEBS Letters*, 1998, pp. 99-103, vol. 436.
Illangasekare, Mali et al., "Aminoacyl-RNA Synthesis Catalyzed By An RNA," *Science*, Feb. 3, 1995, pp. 643-647, vol. 267, No. 5198.
Illangasekare, Mali et al., "Small-Molecule-Substrate Interactions With A Self-Aminoacylating Ribozyme," *J. Mol. Biol.*, 1997, pp. 631-639, vol. 268.
Illangasekare, Mali et al., "Specific, Rapid Synthesis Of Phe-RNA By RNA," *Proc. Natl. Acad. Sci. USA*, May 1999, pp. 5470-5475, vol. 96.
Lee, Nick et al., "Ribozyme-Catalyzed tRNA Aminoacylation," *Nature Structural Biology*, Jan. 2000, pp. 28-33, vol. 7, No. 1.
Lohse, Peter A. et al., "Ribozyme-Catalysed Amino-Acid Transfer Reactions," *Nature*, May 30, 1996, pp. 442-444, vol. 381.
Lorsch, Jon R. et al., "In Vitro Evolution Of New Ribozymes With Polynucleotide Kinase Activity," *Nature*, Sep. 1, 1994, pp. 31-36, vol. 371.
Pan, Tao et al., "In Vitro Selection Of RNAs That Undergo Autolytic Cleavage With $Pb^{2+}$," *Biochemistry*, Apr. 28, 1992, pp. 3887-3895, vol. 31, No. 16.
Piccirilli, Joseph A. et al., "Aminoacyl Esterase Activity Of The Tetrahymena Ribozyme," *Science*, Jun. 5, 1992, pp. 1420-1424, vol. 256, No. 5062.
Prudent, James R. et al., "Expanding The Scope Of RNA Catalysis," *Science*, Jun. 24, 1994, pp. 1924-1927, vol. 264, No. 5167.
Saito, Hirohide et al., "A Ribozyme Exclusively Aminoacylates The 3'-Hydroxyl Group Of The tRNA Terminal Adenosine," *J. Am. Chem. Soc.*, 2001, pp. 7178-7179, vol. 123.
Saito, Hirohide et al., "Concurrent Molecular Recognition Of The Amino Acid And tRNA By A Ribozyme," *RNA*, 2001, pp. 1867-1878, vol. 7.
Suga, Hiroaki et al., "Structural And Kinetic Characterization Of An Acyl Transferase Ribozyme," *J. Am. Chem. Soc.*, 1998, pp. 1151-1156, vol. 120.
Bessho, et al.; A tRNA aminoacylation system for non-natural amino acids based on a programmable ribozyme; Nature Biotechnology, vol. 20, Jul. 2002; pp. 723-728; XP-002374062.
Saito, et al.; An in vitro evolved precursor tRNA with aminoacylation activity; The EMBO Journal, 2001, vol. 20, No. 7; pp. 1797-1806; XP-002430320.

\* cited by examiner

*Primary Examiner*—Janet L Epps-Smith
(74) *Attorney, Agent, or Firm*—Hodgson Russ LLP

(57) ABSTRACT

The present invention provides catalytic RNA molecules having cis or trans aminoacylation activity. The catalytic RNA molecules having cis aminoacylation activity comprise a catalytic domain and an aminoacylation domain. The catalytic RNA molecules having trans aminoacylation activity only have the catalytic domain. A method is provided for constructing and screening of these molecules. These molecules are suitable for aminoacylating with specific amino acids.

20 Claims, 16 Drawing Sheets

Fig. 1A
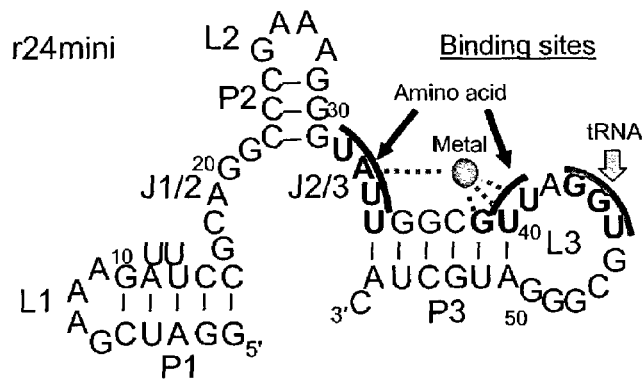
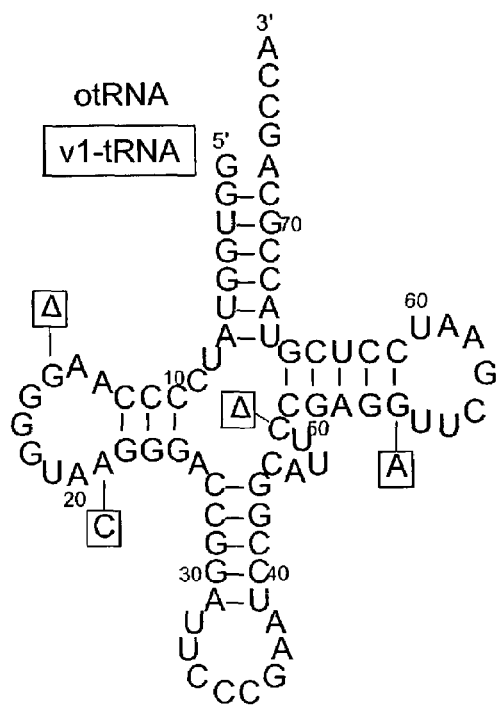
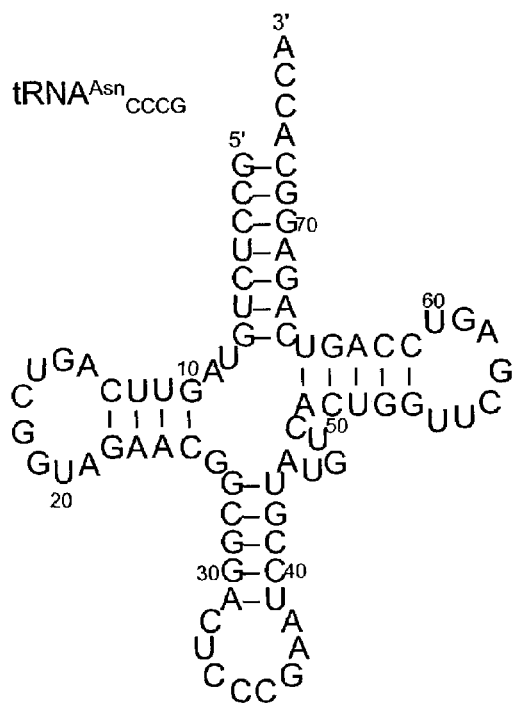
Fig. 1B
Fig. 1C

Fig.4A
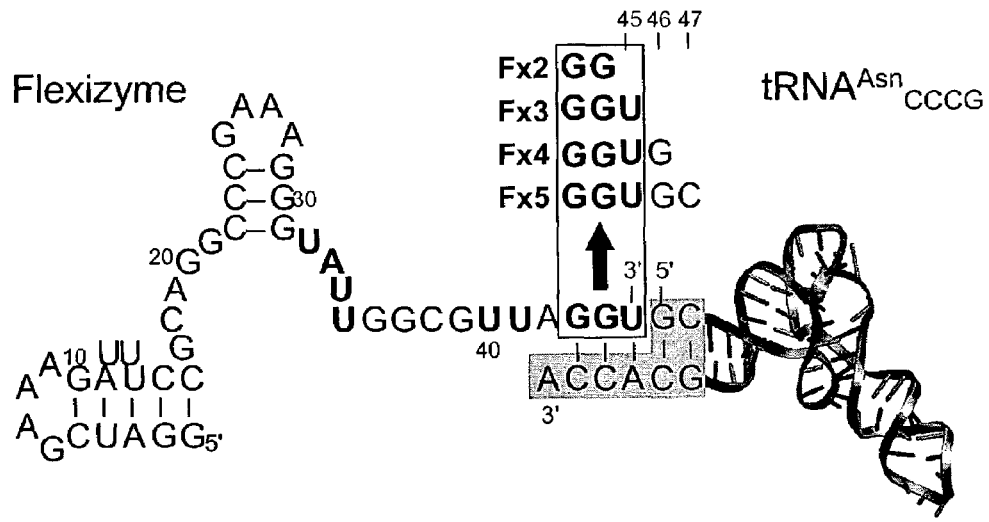
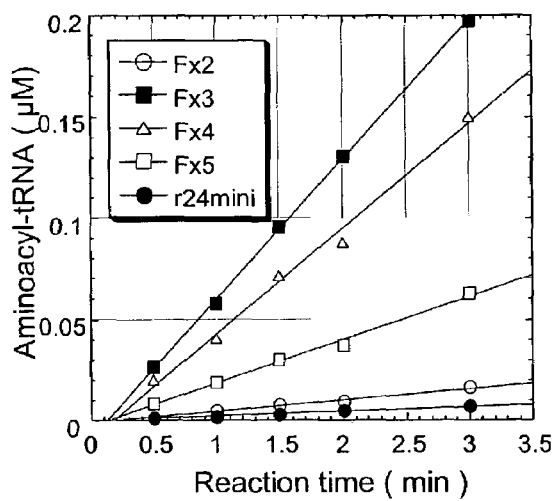
Fig.4B
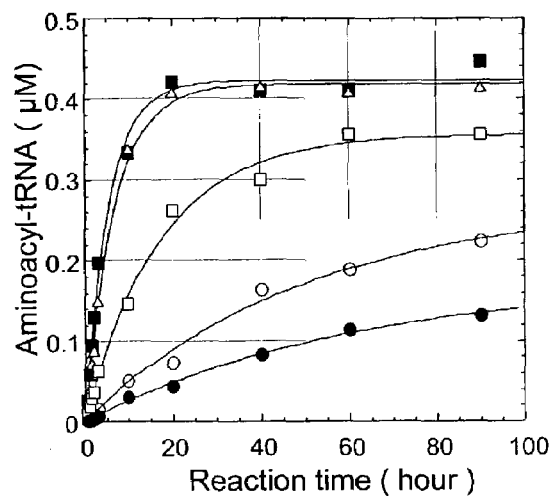
Fig.4C

| Ribozyme | Fx3 | | | | | | | | r24mini | | | | | | | |
|---|---|---|---|---|---|---|---|---|---|---|---|---|---|---|---|---|
| tRNA | fMet | Phe | ot | v1 | Asn | Asn | Asn | Asn | fMet | Phe | ot | v1 | Asn | Asn | Asn | Asn |
| $N_{73}$ | A | A | G | G | A | C | G | U | A | A | G | G | A | C | G | U |
| Yield (%) | 17 | 24 | 11 | 7.3 | 19 | 3.5 | 18 | 4.9 | 1.4 | 1.4 | 4.0 | 8.6 | 1.0 | 0.8 | 0.8 | 0.6 |

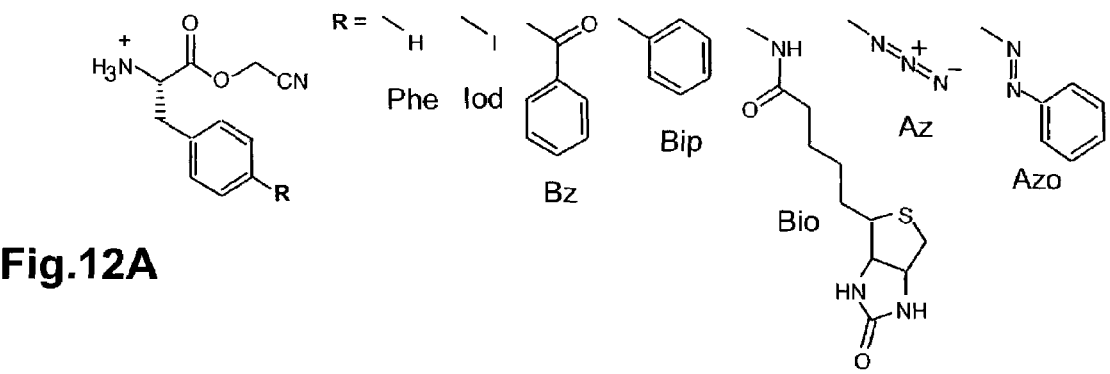
Fig.12A
Fig.12B
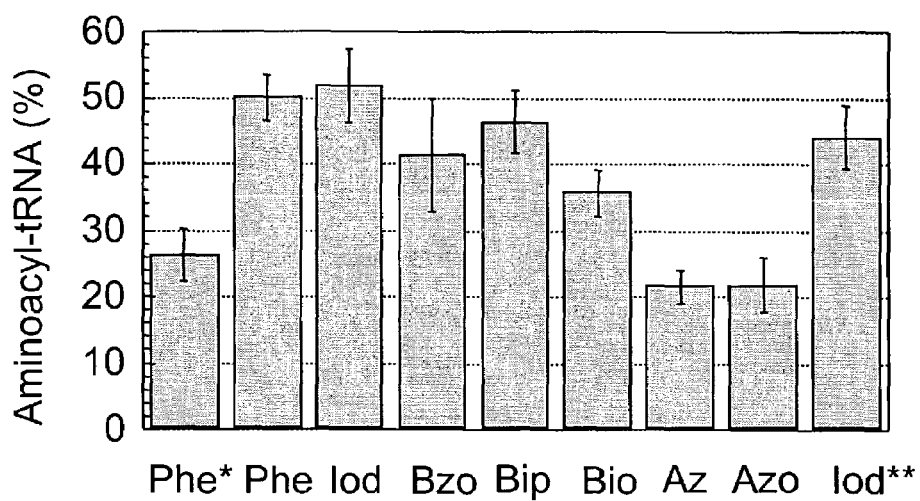
Fig.12C

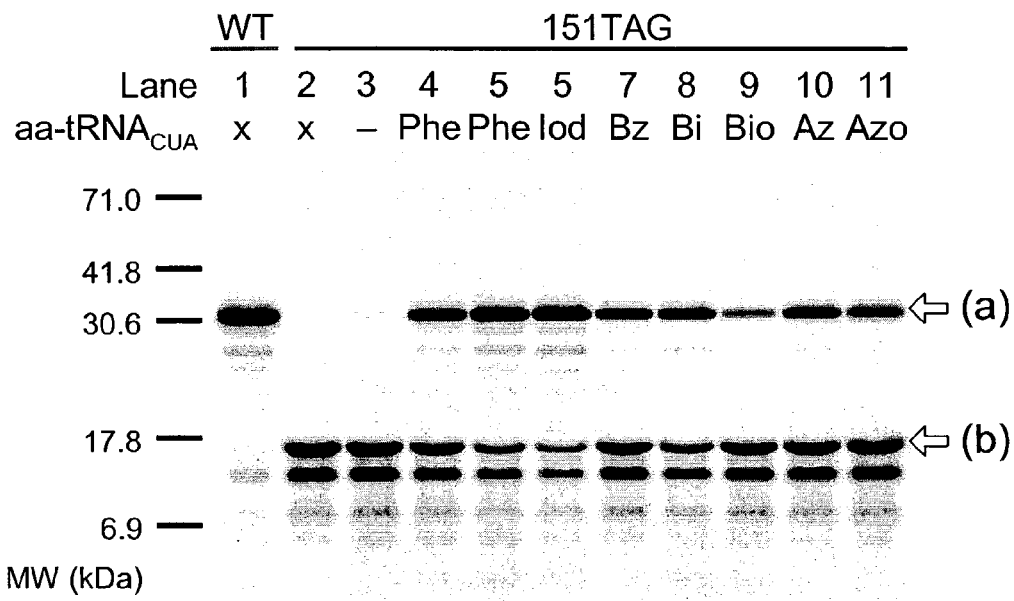
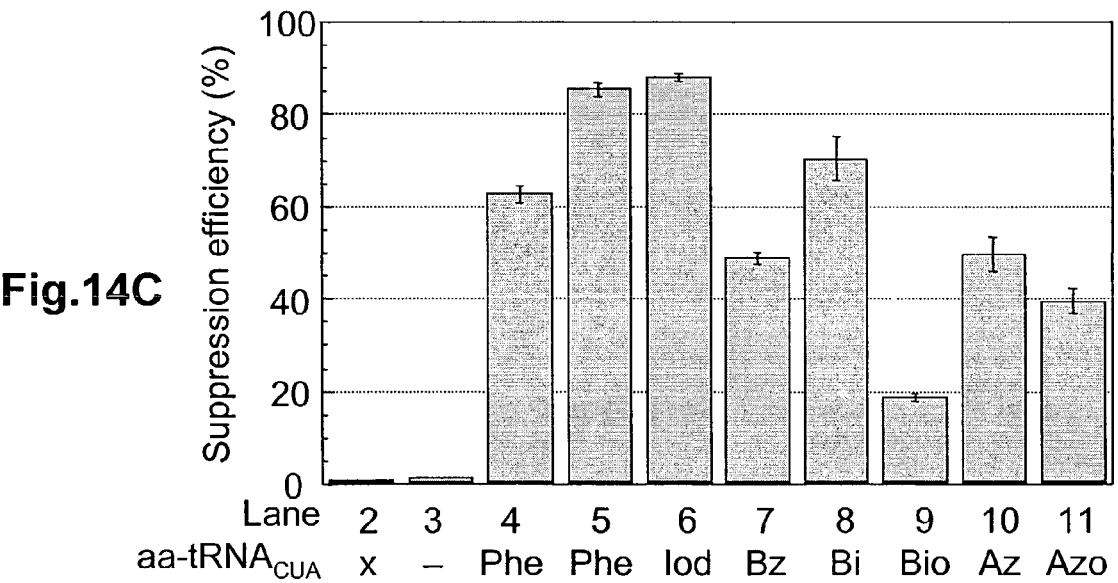

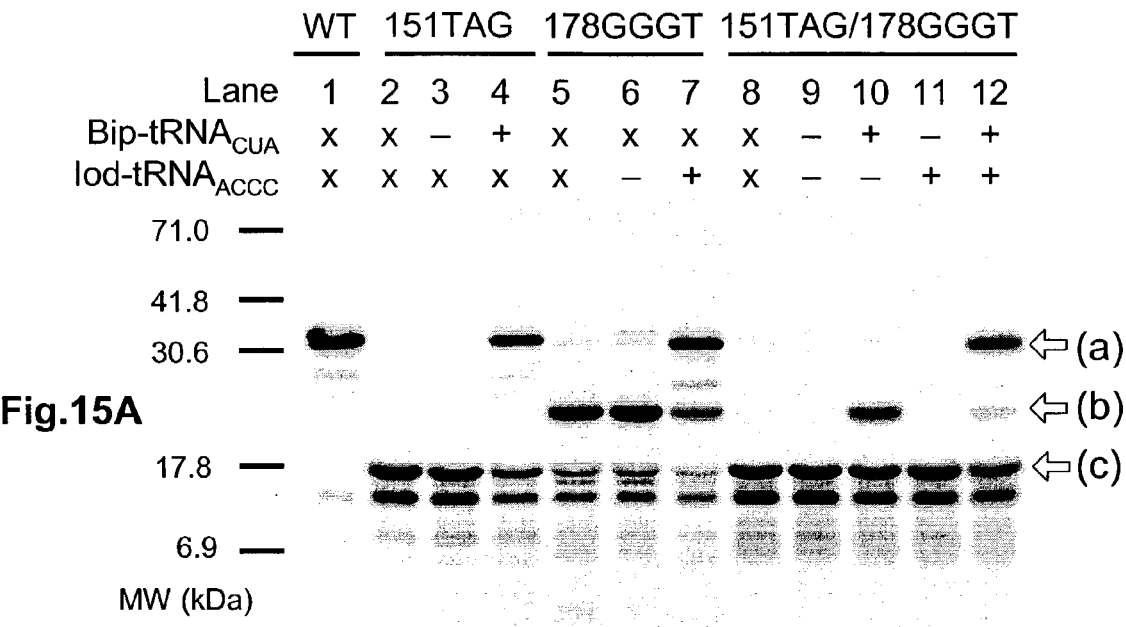
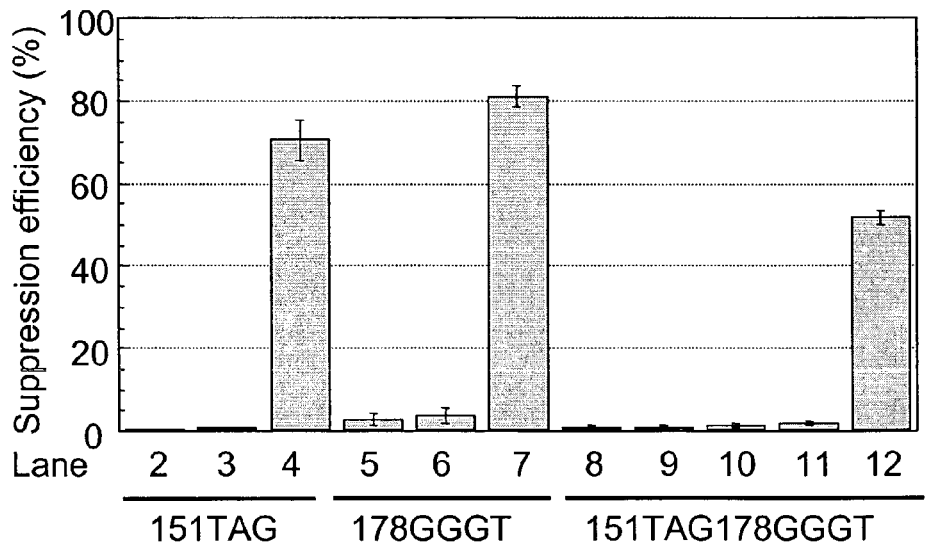
Fig. 15C

Fig.16A
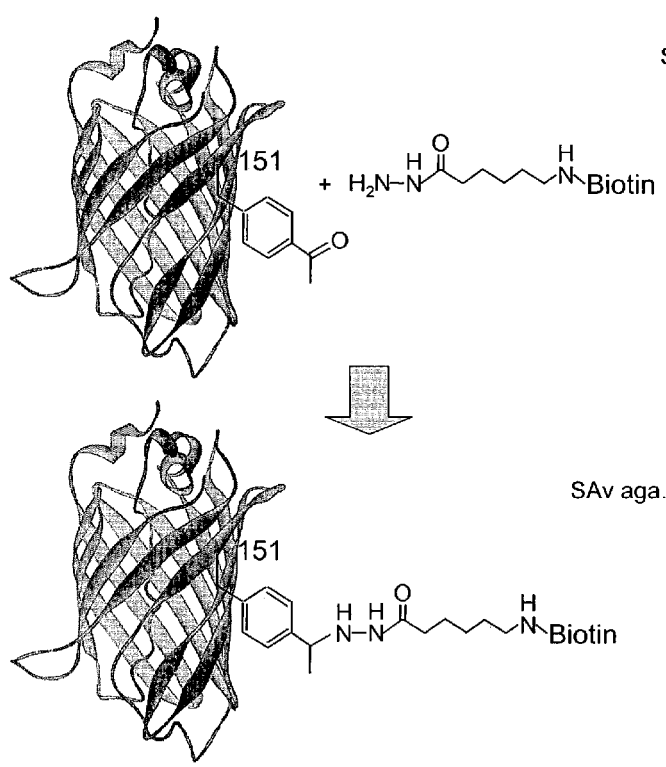
Fig.16B
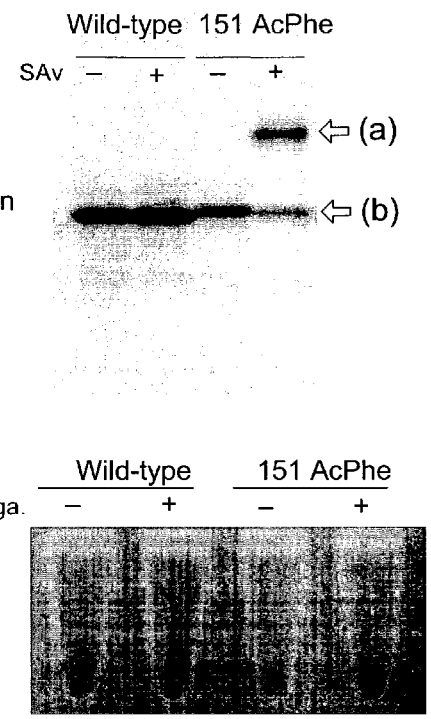
Fig.16C ental application No. 60/357,424 filed on Feb. 15, 2002, the disclosure of which is incorporated herein by reference.

RIBOZYMES WITH BROAD TRNA AMINOACYLATION ACTIVITY

This application claims the priority of U.S. provisional application No. 60/357,424 filed on Feb. 15, 2002, the disclosure of which is incorporated herein by reference.

FIELD OF THE INVENTION

The present invention relates generally to the field of catalytic RNA molecules and in particular to catalytic RNA molecules having the ability to aminoacylate tRNAs.

BACKGROUND OF THE INVENTION

Proteins containing non-natural amino acids hold great promise for biomedical and therapeutic purposes. Such amino acids may be particularly useful in the structural and functional probing of proteins, construction of peptide libraries for combinatorial chemistry, and in proteomics. However, the synthesis of such proteins has been exceptionally costly and inefficient. In the translation system that is known to occur currently in nature, part of the genetic coding mechanism is carried out by aminoacyl-tRNA synthetases (ARSs), which are proteins that charge amino acids onto their cognate tRNAs such that the amino acids are incorporated correctly into growing polypeptide chains by the translational machinery.

ARSs exist in 20 different forms, each of which specifically catalyzes the esterification of a single amino acid to its cognate tRNA isoacceptor, thereby directly connecting the amino acid with its corresponding anticodon triplet. Because mischarging of noncognate amino acids to tRNAs causes miscorporation of amino acids into cellular proteins which can be fatal to their intracellular activity, the fidelity of the aminoacylation reactions by the ARSs must be extremely high. To achieve this important task, the ARSs use very sophisticated mechanisms to selectively recognize the cognate amino acids and tRNAs. The recognition determinants of tRNAs are diverse ranging from the anticodon loop to the acceptor-stem and the phosphate-ribose backbone. Because of these complexities, engineering of ARSs with desired specificities toward non-natural tRNAs and amino acids has not been achieved. As a result, attention has turned to nucleic acids.

For many years, nucleic acids were considered to be only informational molecules. However, the pioneering work of Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. For example, RNAs have been reported to catalyze phosphodiester cleavage on DNA (Beaudry et al., 1992, Science, 257: 635), hydrolysis of aminoacyl esters (Piccirilli et al., 1992, Science, 256:1420-1424), self-cleavage (Pan et al., 1992, Biochemistry, 31:3887), ligation of an oligonucleotide with a 3'OH to the 5'triphosphate end of the catalyst (Bartel et al., 1993, Science, 261:14111418), biphenyl isomerase activity (Schultz et al., 1994, Science, 264:1924-1927), and polynucleotide kinase activity (Lorsch et al., 1994, Nature, 371: 31-36).

To identify novel catalysts, Brennen et al. (1992, Proc. Natl. Acad. Sci., U.S.A, 89:5381-5383) constructed a heterogeneous pool of macromolecules and used an in vitro selection process to isolate molecules that catalyze the desired reaction. A variation of this approach has been used by Gold et al. (U.S. Pat. No. 5,475,096). This method, known as Systematic Evolution of Ligands by Exponential enrichment (SELEX), identifies nucleic acids that have the ability to form specific, non-covalent interactions with a variety of target molecules. A related patent (U.S. Pat. No. 5,990,142) is based on the SELEX method, but can potentially identify modified and non-modified RNA molecules that can catalyze covalent bond formation with a target. Recently, a similar approach was used to identify catalytic RNA molecules having phosphodiesterase and amidase activity (U.S. Pat. No. 6,063,566 to Joyce).

Additionally, studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381: 442-444). The predominant method for the in vitro synthesis of aminoacyl-tRNAs currently relies on chemical aminoacylation of a dinucleotide followed by enzymatic ligation to an engineered tRNA fragment. These steps are unfortunately time consuming and laborious (Heckler et al., Biochemistry, 1984 (23) 1468-1473). Thus, there is a need for a method for the aminoacylation of tRNAs wherein any tRNAs of choice can be aminoacylated with desired amino.

SUMMARY OF THE INVENTION

The present invention provides catalytic RNA molecules that can aminoacylate tRNAs. These catalytic RNA molecules can be used to aminoacylate tRNAs with desired natural or non-natural amino acids.

The present invention also provides a method of constructing such catalytic RNA molecules. This method comprises the steps of building separate pools of partially randomized ribozyme sequences, performing directed evolution on the pools, screening the pools for the desired aminoacylation activity and selecting and characterizing sequences with the desired aminoacylation activity.

The present invention also provides a method for using the catalytic RNAs for making aminoacylated tRNAs according to the present invention. The method comprises the steps of providing catalytic RNA molecules, contacting the catalytic RNA molecules with the desired natural or non-natural amino acids and with the tRNAs, and isolating the aminoacylated tRNAs.

Further, the present invention provides a method for using the aminoacylated tRNAs aminoacylated with non-cognate tRNAs in protein translations for making polypeptides having desired amino acids (natural or non-natural) incorporated at selected positions. The method comprises the steps of providing an mRNA having an identified or engineered codon at selected positions, providing tRNAs aminoacylated with the desired natural or non-natural amino acids wherein the tRNAs have anticodons corresponding to the identified or engineered codons of the mRNA, and combining the mRNA and aminoacylated tRNAs or with a translation system such that the desired natural or non-natural amino acid is incorporated at the selected positions in the polypeptide made from the mRNA.

The present invention provides a ribozyme having a broad aminoacyl tRNA synthetic activity. This ribozyme can aminoacylate tRNAs with non-cognate amino acids and with non-natural amino acids.

The present invention also provides a tRNA molecule which is aminoacylated with a non-cognate amino acid which can be used in translation system to synthesize polypeptides having desired amino acid (natural or non-natural) at selected positions.

The present invention also provides kits for making tRNAs aminoacylated with non-cognate amino acids and for making polypeptides containing desired amino acids (including non-natural amino acids) at selected positions.

BRIEF DESCRIPTION OF THE FIGURES

FIG. 1A shows r24mini (SEQ ID NO:1). The amino acid binding site, tRNA binding site and metal binding site are indicated. The tRNA binding site (G43-U45) of r24mini forms base pairs with $G_{73}$-$C_{75}$ of v1-tRNA.

FIG. 1B shows otRNA (SEQ ID NO:2) and v1-tRNA (SEQ ID NO:3) (rectangles). The rectangle boxes indicate mutations and deletions (Δ) found in v1-tRNA.

FIG. 1C shows tRNA$^{Asn}_{CCCG}$ (SEQ ID NO:4). Bases in all tRNAs are numbered according to the tRNA numbering rule (Sprinzl, M. et al. *Nucleic Acids Res.*, 26, 148-153 (1998)).

FIG. 4A shows a series of ribozyme derivatives Fx2 ribozyme (SEQ ID NO:29), Fx3 ribozyme (SEQ ID NO:30), Fx4 ribozyme (SEQ ID NO:31) and Fx5 ribozyme (SEQ ID NO:32). The conserved bases found in the studies on r24mini are highlighted in bold (see also FIG. 1A). The 3'-end of the ribozyme, which is complementary to the 3'-end of tRNA ($A_{73}$-$C_{75}$), was manipulated in each construct to form additional base pairs (Fx4 ribozyme and Fx5 ribozyme) or lack one base pair (Fx2 ribozyme) as shown.

FIG. 4B shows a comparison of the initial rates between ribozymes (Fx2-5 ribozymes) and r24mini. Data obtained in 0.5-3 min were fit to a linear plot. The observed rates were 5.8, 69, 52, and 21 nM/min for Fx2 ribozyme-5, respectively, and 2.4 nM/min for r24mini.

FIG. 4C shows a comparison of the ribozyme activities in 0.5-90 min. Data were fit to the first-order kinetic equation, which gave virtually same values as those derived from the linear plots. In these experiments, reactions were carried out in presence of 1 μM tRNA$^{Asn}_{CCCG}$, 2 μM ribozyme, and incubated with 5 mM Biotin-Phe-CME at 25° C., and amounts of the aminoacyl-tRNA product were determined by streptavidin gel shift assay. Plots symbols are the same as for FIG. 4B.

FIG. 12A shows examples of cyanomethyl activated amino acids used in this study. These amino acids have various groups at the p-position of phenyl ring.

FIG. 12B shows aminoacylation analysis by streptavidin (SAv)-dependent gel-shift assay. Amino acid specific biotinylation was done after an aminoacylation reaction to detect an aminoacyl-tRNA. (a) indicates the shifted, aminoacylated tRNAs; (b) indicates unshifted, unaminoacylated tRNAs.

FIG. 12C shows aminoacylation efficiency for amino acids of FIG. 12A. The middle of the error bar represents the mean score form 3 different trials. The error bar represents a standard deviation of all trials. Abbreviations: (a), Aminoacyl-tRNA-streptavidin complex; (b), unaminoacylated tRNA; *, aminoacyl-tRNA containing dC75, which was prepared by the chemical aminoacylation method; **, tRNA that has a ACCC 4-base anticodon (SEQ ID NO:50) instead of CUA anticodon; Phe, phenylalanine; Iod, p-iodophenyalanine; Bzo, p-benzoylphenyalanine; BiPhe, p-biphenyalanine; Bio, p-biotynyl-aminophenylalanine; Az, p-azidophenyalanine; Azo, p-phenylazophenylalane.

FIG. 14A shows SDS-PAGE analysis of translation reaction. Lane 1, wild type; lane 2, no suppressor tRNA was added; lane 3, suppressor tRNA was added; lane 4, chemically synthesized Phe-tRNA containing dC75 was added; lane 5-11, aminoacyl-tRNA prepared by the ribozyme-resin was added. Abbreviations: aa-tRNA, aminoacyl-tRNA; x, no tRNA; –, no aa-tRNA; +; aa-tRNA; (a), full-length protein; (b), truncated peptide. A band below (b) is an unknown truncated peptide, which exists in the translation for not only the mutant proteins but also wild type.

FIG. 14B shows fluorescence activity of each GFP, analyzed by Molecular Imager FX.

FIG. 14C shows suppression efficiency. The middle of the error bar represents the mean score form 3 different trials. The error bar represents a standard deviation of all trials.

FIG. 15A shows SDS-PAGE analysis of translation reaction with site-specific incorporation of two non-natural amino acids using 178GGGT and 151TAG/178GGGT mutants. Abbreviations: x, no tRNA; –, no aa-tRNA; +; aa-tRNA; (a), full-length protein; (b), truncated peptide at position 180 (failed frame shift); (c) truncated peptide at position 151 (amber stop codon).

FIG. 15B shows fluorescent activity of each GFP, analyzed by Molecular Imager FX.

FIG. 15C shows suppression efficiency. The middle of the error bar represents the mean score form 3 different trials. The error bar represents a standard deviation of all trials.

FIG. 16A shows a schematic representation of post-translation biotin modification of GFP. AcPhe (p-acetylphenylalanine) was incorporated at position 151. The ribozyme-resin-catalyzing tRNA aminoacylation efficiency using the AcPhe substrate was 45% determined by SAv-dependent gel-shift assay, and the suppression efficiency was 40% determined by SDS-PAGE (data not shown). After protein purification, the keto group of 151 AcPhe was modified by biotin-LC-hydrazide.

FIG. 16B shows SAv-dependent gel-shift assay of wild type and biotinylated 151 AcPhe mutant GFPs. An approximately 80% of the mutant GFP band was retarded by the addition of SAv, whereas no shift was observed for wild type.

FIG. 16C shows SAv-agarose (aga) capture of the mutant GFP. SAv-agarose to the biotinylated mutant GFP successfully captured the GFP and concentrated it on the resin, whereas no capture was observed for wild type.

DETAILED DESCRIPTION OF THE INVENTION

Figure 2A:
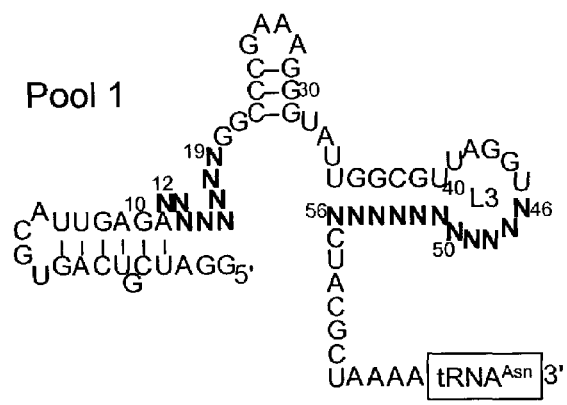
FIG. 2A shows Pool 1 (SEQ ID NO:5). The introduced random bases are shown in N. The base numbering was kept the same as that of r24mini, while 9 nucleotides were inserted in the P1 stem in order to present enough base pair interactions for 5'-primer annealing.

The term "ribozyme" as used herein for the purposes of specification and claims is interchangeable with "catalytic RNA" and means an RNA molecule that is capable of catalyzing a chemical reaction.

The term "cognate natural amino acid" or "cognate amino acid" as used herein for the purposes of the specification and claims means the amino acid with which a tRNA is normally charged in vivo.

The term "non-cognate amino acid" as used herein for the purposes of the specification and claims means any amino acid with which a tRNA is not normally aminoacylated and includes any amino acid aminoacylated onto a tRNA having a stop codon or a four base codon. The term "non-cognate amino acid" for the purposes of the specification and claims does not include biotinylated amino acids. Further, the term "non-cognate amino acid" for the purposes of the specification and claims also describes an amino acid having been incorporated into a polypeptide from an mRNA where the codon corresponding to the amino acid's position in the polypeptide is not the codon which corresponds to the amino acid under the genetic code.

The term "charge" as used herein for the purposes of specification and claims is used interchangeably with "aminoacylate".

The term "natural amino acid" as used herein for the purposes of the specification and claims refers to any amino acid among the twenty amino acids that are normally aminoacylated onto tRNAs in living cells. Such amino acids are alanine, valine, leucine, isoleucine, proline, tryptophan, phenylalanine, methionine, glycine, serine, threonine, tyrosine, cysteine, glutamine, asparagine, lysine, arginine, histidine, aspartic acid, and glutamic acid.

The term "non-natural amino acids" as used herein for the purposes of the specification and claims means amino acids other than those listed above.

The term "tRNA" as used herein for the purposes of the specification and claims refers to an RNA molecule that can adopt a secondary structure similar to the known clover-leaf secondary structure of tRNAs known to be aminoacylated by AARs. Examples of tRNAs include natural tRNAs such as tRNA$^{Phe}$ or tRNA$^{Leu}$ and also include non-natural tRNAs such as artificial orthogonal suppressor tRNA (otRNA) which is derived from an amber suppressor tRNA$^{Gln2}$ but not recognized by bacterial aminoacyl tRNA synthetases (ARSs). Amber suppressor tRNAs derived or isolated from various organisms are additional examples of tRNAs.

The term "polypeptide" as used herein for the purposes of the specification and claims refers to any series of amino acids of two or more amino acids joined by peptide bonds.

The present invention provides a ribozyme capable of aminoacylating any tRNAs with non-natural and natural amino acids. In one embodiment, the ribozyme comprises a GGU motif and a U-rich region. Compared to the structure of the r24mini (FIG. 1A) the ribozyme of the present invention has fewer predicted stems and a shorter sequence. Although not intending to be bound by any particular theory, it is believed that the U-rich region (bases 32-35) is responsible for the recognition of the amino acid substrate and a GGU-motif (bases 43-45) forms base pairs with tRNA 3' termini, allowing recognition of both the amino acid and tRNA simultaneously and facilitating the aminoacylation of the 3'terminus of tRNA in trans. Additionally, the GGCG (SEQ ID NO:61) (bases 36-39) sequence is believed to be important for the ribozymes' activity. However, unlike previously disclosed catalytic RNAs, the present ribozyme's sequences result in the ability to catalyze reactions between a broader spectrum of tRNAs and non-natural amino acids. This is useful for making tRNAs aminoacylated with non-natural amino acids for use in in vitro translation reactions.

The ribozymes of the present invention were generated by in vitro selection using a partially randomized r24mini (FIG. 1A) conjugated with tRNA$^{Asn}_{CCCG}$ (FIG. 1C), followed by systematic engineering of a consensus sequence found in the active clones (see FIG. 3) in a manner that will be more fully appreciated through the Examples herein. These ribozymes, and in particular Fx3 ribozyme (see FIG. 4A) can act as a versatile catalyst for the synthesis of various aminoacyl-tRNAs charged with desired natural and non-natural amino acids including an array of Phe analogs.

The present invention also provides a tRNA which is aminoacylated with a non-cognate amino acid including natural amino acids. While the ribozymes of the present invention can be used to aminoacylate tRNAs in solution in a manner that will be understood more fully by way of the Examples herein, the present invention further provides a substrate-immobilized form of ribozyme that can aminoacylate tRNAs and enable efficient affinity purification of the aminoacylated products. Examples of suitable substrates include agarose, sepharose, and magnetic beads. For example, ribozymes can be immobilized on resins by taking advantage of the chemical structure of RNA. Periodate oxidation of the 3'-cis-diol on the ribose of RNA yields the corresponding dialdehyde, and this functional group allows the immobilization of the RNA on the resin. Various types of resins can be used including inexpensive hydrazide resins wherein reductive amination makes the interaction between the resin and the ribozyme an irreversible linkage. The resin can be recycled multiple times by for example, equilibration of the ribozyme-resin with the reaction buffer. Thus, the synthesis of aminoacyl-tRNAs can be significantly facilitated by this on-column aminoacylation technique.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0)

The aminoacylated tRNAs of the present invention can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially (see below).

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System® (RTS®) (Roche®, Inc.). The RTS® utilizes a coupled transcription/translation system wherein expression of a polypeptide from an input DNA template is enabled. The system includes a mixture containing *E. coli* lysate for providing translational components such as ribosomes and translation factors. Additionally, an RNA polymerase is included for the transcription of the input DNA into an mRNA template for use in translation. An example of such a polymerase is T7 RNA polymerase. Further, the RTS® can use compartmentalization of the reaction components by way of a membrane interposed between reaction compartments, including a supply/waste compartment and a transcription/translation compartment. Because of the membrane-based separation of the coupled transcription/translation reactions from the metabolic byproducts of the transcription/translation, the yield of protein is increased because of mitigation of inhibition of the reactions by the reactions' byproducts.

By combining a translation system with an mRNA containing codons or designed to have codons complementary to the anticodons of the tRNAs aminoacylated by the ribozymes of the present invention, the translation system can incorporate non-natural amino acids at any pre-selected position in a polypeptide. As an example of non-natural amino acid incorporation into a pre-selected position into a polypeptide not meant to be limiting in any way, a hypothetical polypeptide of 100 amino acids with a non-natural amino acid at position 50 may be made as follows.

An mRNA designed to bear a codon at position 50 that is complementary to the anticodon of a tRNA aminoacylated with a non-natural amino acid by a ribozyme of the present invention is added to a translation system. The mRNA may be transcribed from a DNA template using any of a variety of transcription protocols well know to those skilled in the art. For additional details regarding transcription, see for example Sambrook et al., Molecular Cloning, Cold Spring Harbor Laboratory Press (1990). As an example, the mRNA may be transcribed using a prokaryotic RNA polymerases such as T7 RNA polymerase. The DNA template may be a linearized double stranded DNA made by the polymerase chain reaction (PCR), or made by annealing two chemically synthesized complementary DNA strands together, or by linearizing a plasmid. The DNA template may also be an intact plasmid. An example of a commercially available plasmid is the pGEM7Z® plasmid. The DNA template has a transcription promoter recognized by the RNA polymerase of choice. The region of the DNA to be transcribed includes one or more open reading frames comprised of codons. The codons comprise amino acid codons selected from the genetic code and may further comprise non-sense, mis-sense and non-natural codons such as four-base codons. In order to introduce the non-natural amino acid into the polypeptide, the DNA template is designed to encode an mRNA that will bear a codon that pairs with the anticodon of an aminoacyl-tRNA aminoacylated with ribozyme of the present invention. By way of illustration not meant to be limiting in any way, such a codon may be an amber codon having the sequence UAG. The UAG amber codon in an mRNA signals termination of translation.

For the hypothetical 100 amino acid polypeptide, translating an mRNA transcribed from a DNA template encoding an mRNA bearing an amber codon at position 50 in an otherwise open reading frame of 100 amino acids results in a predicted polypeptide of 49 amino acids due to termination of translation at the amber codon at position 50. However, a different result is reached by the addition of an aminoacylated tRNA having an anticodon complementary to the amber codon. By using a ribozyme of the present invention, a tRNA having an anticodon complementary to the amber stop codon can be aminoacylated with a non-natural amino acid and added to a translation programmed with the mRNA bearing the amber codon at position 50. In this way, instead of translation termination at the amber codon, the non-natural amino acid or desired natural amino acid on the tRNA aminoacylated by a ribozyme of the present invention is incorporated into the polypeptide at position 50 and translation is able to proceed through the remaining 50 codons of open reading frame. Moreover, the use of the combination of two suppressor tRNAs, each of which contains amber or 4-base codon, allows the incorporation of two different non-natural amino acids into two pre-selected positions (See FIG. 15).

Figure 11A:
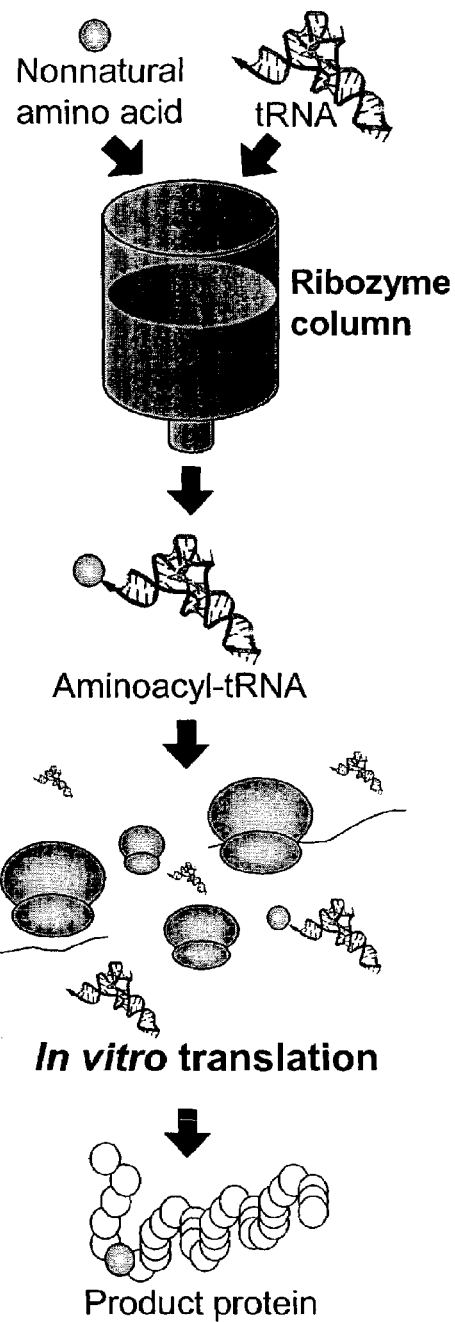
FIG. 11A shows a schematic representation of incorporation of a desired amino acid at a selected position in a polypeptide.
Figure 11B:
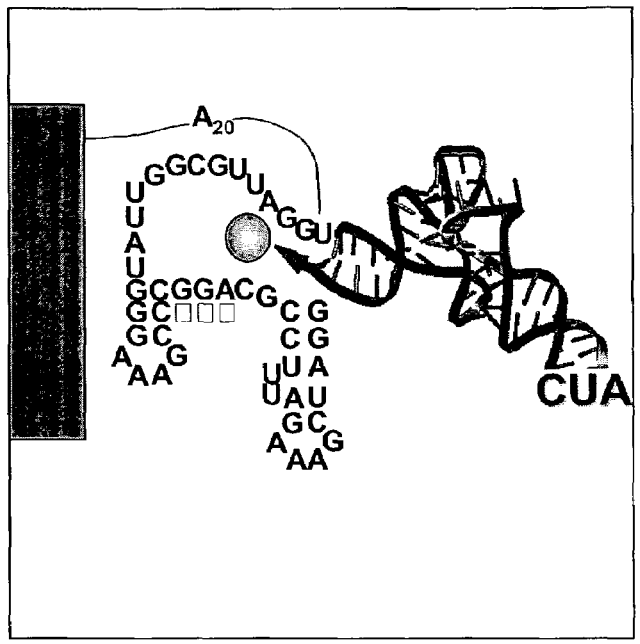
FIGS. 11B and 11C show a schematic representation of aminoacylation of tRNA. The aminoacyl-tRNA product is added to in vitro transcription-translation coupled system with a mutant gene. The mutant gene contains amber codon at a specific position. An amber suppresser tRNA suppresses the amber codon and incorporates a non-natural amino acid. The sequence of the ribozyme depicted in FIG. 11B is provided as SEQ ID NO:30.
Figure 11C:
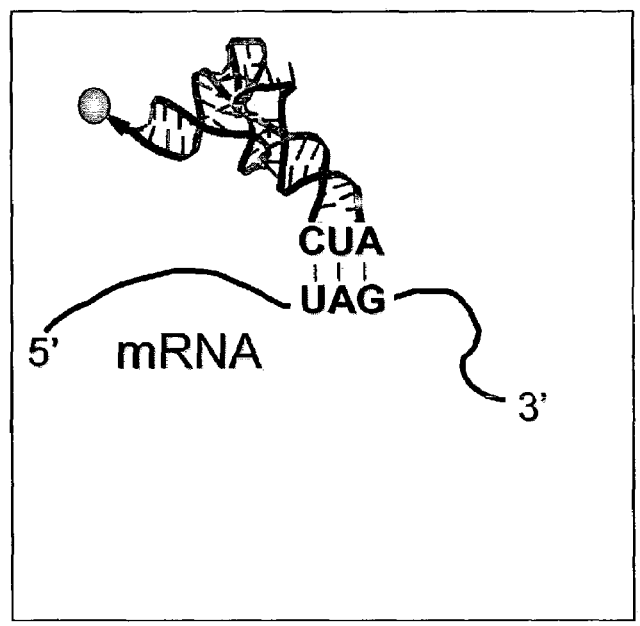

The hypothetical example is shown schematically in FIGS. 11A-C using a ribozyme of the present invention. FIG. 11A demonstrates the synthesis of an aminoacyl-tRNA with a non-natural amino acid by adding an amino acid substrate and tRNA into a column which contains a resin-immobilized ribozyme of the present invention as describe in the preceding Example. In FIG. 11B, the aminoacyl-tRNA product is added to an vitro transcription-translation coupled system designed to transcribe a gene containing an amber codon at a specific position. An amber suppresser tRNA suppresses the amber codon and incorporates the non-natural amino acid at the amino acid position in the polypeptide that corresponds with the amber codon. Alternatively, a 4-base codon and 4-base suppresser tRNA pair can be used, and a non-natural amino acid is incorporated by "programmed frame shift suppression" (see FIG. 13, codon 178). Programmed frame shift suppression refers to the ability of the translational machinery to translate through a four-base codon. Absent the aminoacylated 4-base suppresser tRNA, the translation reaction would terminate after the four base codon because it would remain in the "zero reading frame" (which is the reading frame in which the ribosome initiated translation) and encounter a stop codon therein. By reading through the 4-base codon, the ribosome can continue in the "+1" frame, which is the zero reading frame shifted forward one nucleotide starting from with the fourth base of the 4-base codon. When the ribozyme is used to charge various phenylalanine analogs onto a 4-base suppresser tRNA as illustrated, the non-natural amino acid is incorporated into the polypeptide precisely at the polypeptide position corresponding to the 4-base codon.

As an alternative to separately transcribing the DNA templates encoding the mRNA to be used in the translation of polypeptides with modified amino acids, the peptide translation may also be carried out using a coupled transcription translation system. By combining a coupled translation system with a DNA template designed to encode mRNAs bearing codons complementary to the anticodons of aminoacylated tRNAs made by the a ribozyme of the present invention, one may direct the incorporation of selected amino acids, including non-natural amino acids, at any particular position in the polypeptide according to the method described above which will become more clear by way of the Examples described herein.

Any polypeptide is suitable for non-natural amino acid incorporation. An example of a polypeptide that may be designed to have the incorporation of natural or non-natural amino acids at selected positions using the methods and compositions of the present invention is Green Fluorescent Protein (GFP). Examples not meant to be limiting in any way of non-natural amino acids that may be incorporated into any polypeptide using the methods of the present invention include but are not limited to p-benzoyl-phenylalanine (bphe) and p-azophenyl-phenylalanine (aPhe).

These and other embodiments will become more clear from the examples described below, which are to be construed as illustrative and not limiting in any way.

EXAMPLE 1

This embodiment describes the isolation of the ribozymes of the present invention.

Selection reactions. Selection reactions were carried out under the following conditions: 50 µL (100 µL in the first round) of 1 µM RNA pool, 2.5 mM biotin-Phe-CME, in EK buffer [50 mM N-(2-hydroxyethy)piperazine-N'-(3-propane-sulfonic acid); EPPS, 12.5 mM KCl pH 7.5], 100 mM MgCl$_2$ and 5 % ethanol. The procedure is as follows: The pool RNA was heated at 95° C. for 3 min and cooled to 25° C. over 5 min. MgCl$_2$ (100 mM for final concentration) was added, followed by a 5 min equilibration. The reaction was initiated by addition of Biotin-Phe-CME in ethanol:water (1:1), and incubated for 30 min (10 min for 5th and 6th rounds). The reaction was stopped by addition of 2 vol of ethanol, and the RNA was precipitated. The RNA pellet was rinsed with 70% ethanol three times, dissolved into EK2 buffer (50 mM EPPS, 500 mM KCl pH7.5), and then 4 units of RNase inhibiter and 4 µL of streptavidin-agarose were added. The mixture was incubated for 30 min at 4° C., and then the resin was washed 6 times with 100 µL of EK2 buffer, 3 times with 100 µL of 4 M urea, 2 times with 100 µL of water. RNAs that nonspecifically bind to the agarose resin were removed by heating the resin for 30 sec at 95° C. in 100 µL of 20 mM EPPS pH 7.0, followed by washing with 100 µL of water. The resin was added to a 10 µL solution of 1 µM of TR primer, 125 µM dNTPs, 50 mM Tris-HCl pH 8.3, 75 mM KCl, 3 mM MgCl$_2$, 10 mM dithiothreitol (DTT), 0.2 µg of streptavidin, and 50 units of MMLV reverse transcriptase (Promega®, Wis.), and then the whole reaction mixture was incubated for 1 h at 42° C. A PCR buffer containing the 5'- and 3'-primers and Taq DNA polymerase was added to the whole RT mixture (including the resin), and subjected to theremocycling to amplify the cDNA sequence. The amplification was confirmed by electrophoresis on 3% agarose, and the dsDNAs were isolated by standard protocols. In the sixth round of selection, the dsDNAs were cloned into a pGEM-T® vector (Promega®), and the cloned plasmid was harvested for sequencing using standard protocols.

Substrates. Biotin-Phe-CME (α-N-biotinyl-phenylalanine cyanomethyl ester) and Phe-CME (phenylalanine cyanomethyl ester) were synthesized by the same procedure as previously described. bPhe-CME (p-benzoyl-phenyalanine cyanomethyl ester) was synthesized from the N-Boc amino acids by using same procedure as Phe-CME. aPhe-CME (p-azophenyl-phenylalanine cyanomethyl ester) was synthesized from p-amino-phenylalanine according the literature procedures.

Aminoacylation assay. The trans-aminoacylation activities were assayed under the following condition: 5 mM Biotin-Phe-CME, in EK buffer, 500 mM $MgCl_2$ and 15% DMSO (dimethyl sulfoxide) in presence of 1 μM tRNA, 2 μM ribozyme (for turnover analysis, 5 μM tRNA, 0.02-0.5 μM ribozymes were used). The procedure is as follows: The tRNA and ribozyme were dissolved into EK buffer independently, heated at 95° C. for 3 min and cooled to 25° C. over 5 min. $MgCl_2$ (500 mM for final concentration) was added, followed by a 5 min equilibration. The two solutions were then mixed, and incubated for 5 min at 25° C. The reaction was initiated by addition of Biotin-Phe-CME in DMSO, and incubated at 25° C. At each time point, an aliquot of the reaction was ethanol precipitated. The pellet was dissolved into 1 μL of water, and then 4 μL of the loading buffer (0.33 mg/mL streptavidin, 50 mM EDTA, 33 mM piperazine-N'N-bis-[2-ethanesulfonic acid] pH 6.1, 6 M urea) was added to the solution. The solution was heated for 30 sec at 95° C., and then cooled to 25° C. The resulting solution was analyzed by 6% denaturing PAGE, running in a cold room in order to keep the gel temperature <20° C. Under these conditions, the streptavidin-biotin complex is stable to retard the aminoacyl-tRNA band, but the RNA structure is denatured.

The trans-aminoacylation activities in the presence of Phe-CME, bPhe-CME, and aPhe-CME were assayed under the following conditions: 10 mM amino acid substrates in EK buffer pH 7.0, 500 mM $MgCl_2$ (in the case of bPhe-CME 5% ethanol was added to avoid its precipitation) in presence of 1 μM tRNA, 2 μM ribozyme. The remaining procedure is similar to that for Biotin-Phe-CME, except for the reaction temperature (on ice instead of 25° C.) and the post-biotinylation according to the following procedure: After 2 h incubation on ice, the reaction was stopped by addition of 2 volumes of ethanol, and then the RNA was precipitated. The pellet was dissolved in 2.5 μL of EPPS (0.1 M, pH 5.9), 20 mM biotin-3-sulfo-N-hydroxysuccinimide ester at 0° C., and then 0.86 μL of EPPS-KOH (0.3 M, pH 9.1) was added to this solution, which brought the pH to 8.0. After 1 hour, the reaction was terminated by ethanol precipitation. The pellet was dissolved in water and analyzed by streptavidin-dependent gel-shift assay as described.

Preparation of ribozymes and tRNAs. The cDNA sequence of each ribozyme (Fx2 ribozyme -Fx5 ribozyme) are shown in FIG. 4A. The cDNA sequence of each ribozyme was chemically synthesized and purified by 6% denaturing PAGE. Each cDNA was annealed with the 5'-primer (5'-GGTAA-CACGC ATATGTAATA CGACTCACTA TAGGATCGAA AGATTTCCGC-3'; (SEQ ID NO:37) and extended by Taq DNA polymerase. The resulting dsDNA was transcribed in vitro using T7 RNA polymerase. The transcript was purified on 6% denaturing PAGE, and isolated by elution from the sliced gel(s) to 0.3 M NaCl followed by ethanol precipitation. Similarly, the tRNA dsDNA template was prepared from the corresponding synthetic cDNA and 5'-primer oligonucleotides, and transcribed in vitro in the presence of 7.5 mM GMP and [α-$^{32}$P]UTP or [α-$^{32}$P]GTP to prepare the body-radiolabeled 5'-P-tRNA molecule (FIGS. 1A and B).

Results

Previous studies on the structure-function relationship of r24 (Saito et al., RNA 2001 December;7 (12):1867-78) determined the essential catalytic core of ribozyme lay in the vicinity of J2/3 and L3 (FIG. 1A). Based on chemical modification and NAIM (nucleotide analog interference mapping) data, it appears that U32-U35 and U40-U41 (referred to as U-rich region) consist of the Phe binding site (FIG. 1A). Moreover, the chemical mapping together with compensatory mutations corroborated the base pairing interaction between G43-U45 and G/A/$U_{73}$-$C_{75}$ (lower case letter refers to the number of tRNA bases). However, if only the above base pairing interaction between the ribozyme and tRNA dictates the binding, it cannot explain the observation that r24mini aminoacylates v1-tRNA more efficiently than it aminoacylates otRNA or tRNA$^{Asn}_{CCCG}$.

Figure 2B:
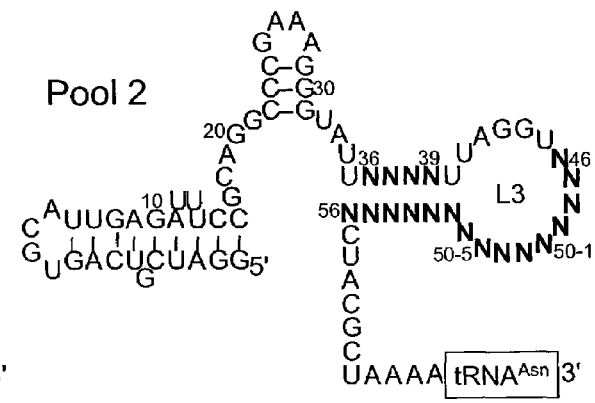
FIG. 2B shows Pool 2 (SEQ ID NO:6). This pool has an insertion of 4 bases into the 46-56 region, shown as 50-X (X=2-5). Otherwise, the same design as for pool 1 was applied.
Figure 2C:
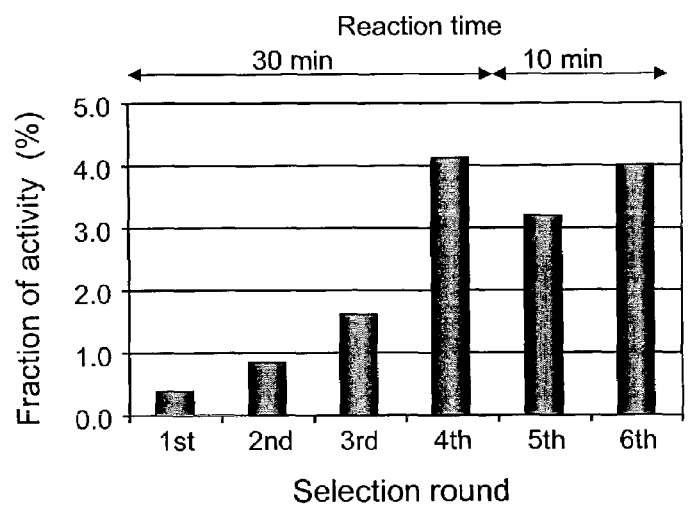
FIG. 2C shows progress in enrichment of the active population during the course of selection. Y-axis of the graph shows the fraction of activity determined by the scintillation count of $^{32}$P retained on the streptavidin agarose divided by a total input $^{32}$P of RNAs.

In order to educate r24mini and develop ribozymes with greater utility evidenced by higher activity toward other tRNAs, we designed RNA pools based on the r24mini sequence containing randomized bases at certain regions. The amino acid and tRNA binding sites were left intact (except for G39) to avoid significant loss of activity in the pool. We also searched all possible sequence space in the pool, and therefore implemented only 19 nucleotides (nt) random sequence in the pool (its complexity is 2.8×10$^{11}$). Based on these considerations, we prepared two pools that have random sequences in different regions (FIG. 2).

Pool construction. The following oligonucleotides containing random sequence (N) were chemically synthesized: P1 (5'-GGATCGTCAG TGCATTGAGA-N8-GGC-CCGAAAG GGTATTGGCG TTAGGT-N11-ACT-ACGCTAA AAGCCTCTGTA GTTCAGTCGG T-3'; (SEQ ID NO:7), P2 (5'-GGATCGTCAG TGCATTGAGA TTTC-CGCAGG CCCGAAAGGG TATT-N4-TTAGGT-N15-ACT-ACGCTAA AAGCCTCTGT AGTTCAGTCG GT-3'; (SEQ ID NO:8), T7 (5'-GGTAACACGC ATATGTAATA CGACT-CACTA TAGGATCGTC AGTGCATTGA GA-3'; (SEQ ID NO:9) (T7 promoter sequence is italicized), TR (5'-TGGT-GCCTCT GACTGGACTC GAACCAGTGA CATACG-GATT CGGGAGTCCG CCGTTCTACC GACTGAACTA CAGAGGC-3'; (SEQ ID NO:10), TR3 (5'-TGGTGCCTCT GACTGGACTC-3'; (SEQ ID NO:11). A 200 μL scale of Taq DNA polymerase extension using the DNA templates of P1 (20 pmol) or P2 (20 pmol) and TR (20 pmol) was performed with a thermocycle of 95° C. for 2 min, 50° C. for 2 min and 72° C. for 10 min. The resulting full-length product was then diluted to 1 mL and subjected to 6 cycles of PCR amplification (95° C. for 1 min, 55° C. for 1 min and 72° C. for 1 min) in the presence of the T7 and TR3 primers. After phenol-chloroform extraction and ethanol-precipitation, each PCR product was quantified, and 10 pmol of each DNA pool was mixed. This mixture of the DNA pools was in vitro transcribed in the presence of [α-$^{32}$P]UTP, and the RNA transcripts were purified by 6% denaturing PAGE.

In pool 1 (FIG. 2A), random bases were introduced at bases 12-19 and 46-56 (note that the base numbering is the same as r24mini, while the P1 stem was extended in order to present enough length for annealing of the 5'-primer). The former random region was designed to address questions whether the bulged U21 and U22 as well as bases at J1/2a play important roles in contributing to the activity. The latter region was designed to investigate whether sequences in downstream of the tRNA binding site are able to increase activity. In pool 2, random bases were implemented into bases 36-39 and 46-56 including 4 bases insertion in L3 (50-2-50-5). Because the bases 36-39 in the part of P3 were flanked between two essential regions of the amino acid binding site, randomizing this region was designed to examine the necessity of this particular sequence. It is also that because their counter bases in P3 (52-55) were randomized, this random region gave a chance to find alternated pairs in P3. To increase the possibility that the selected cis-acting ribozymes can also function in trans, we designed a long 10-base linker, where the sequence was designed based on the sequence previously selected (6 bases) with four additional adenines. This linker was tested using the r24min-linker-v1-tRNA prior to constructing the pool, and the wild type activity of this construct was confirmed. Thus, we synthesized these two pools that were conjugated with $tRNA^{Asn}_{CCCG}$ via the 10-base linker.

Figure 3:
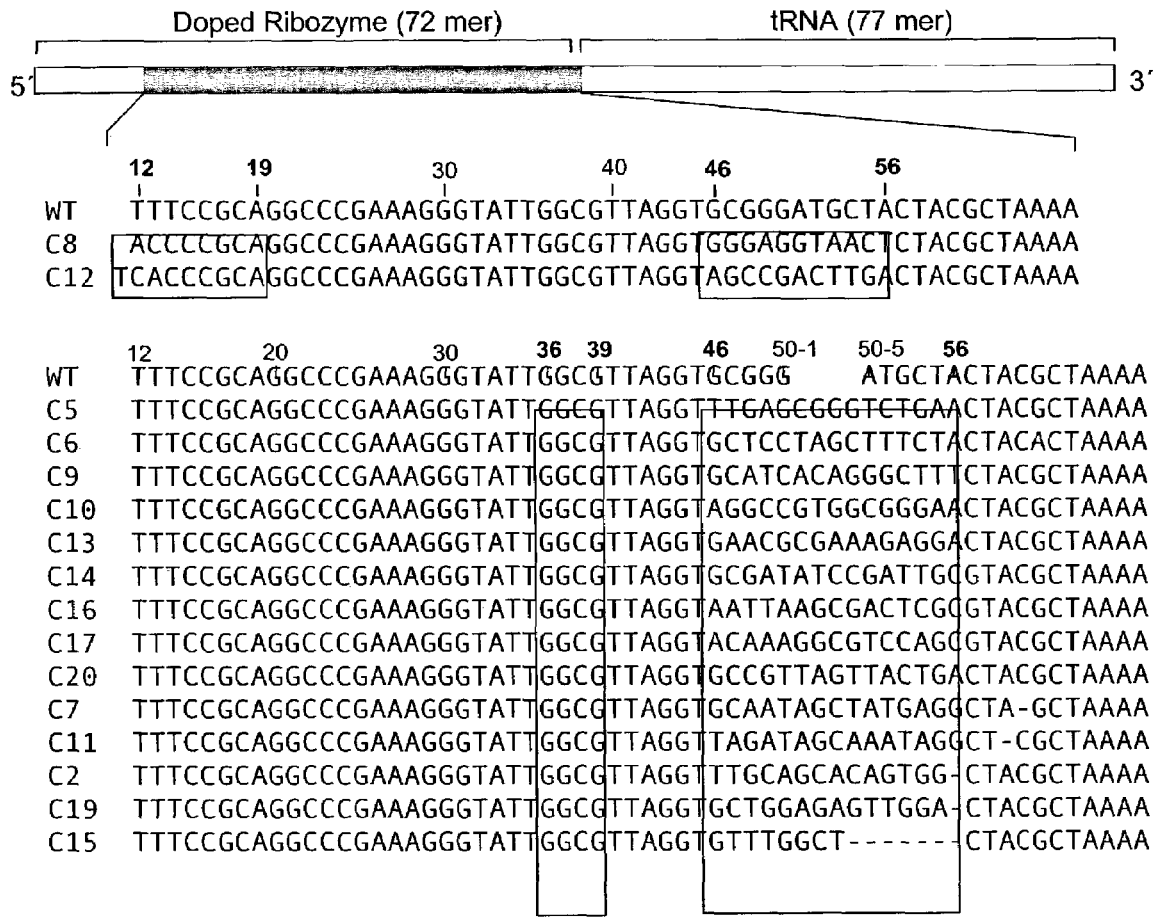
FIG. 3 shows Sequence alignment of wt (SEQ ID NO:12) with the active clones c8 (SEQ ID NO:13), c12 (SEQ ID NO:14), c5 (SEQ ID NO:15), c6 (SEQ ID NO:16), c9 (SEQ ID NO:17), c10 (SEQ ID NO:18), c13 (SEQ ID NO:19), c14 (SEQ ID NO:20), c16 (SEQ ID NO:21), c17 (SEQ ID NO:22), c20 (SEQ ID NO:23), c7 (SEQ ID NO:24), c11 (SEQ ID NO:25), c2 (SEQ ID NO:26), c19 (SEQ ID NO:27), and c15 (SEQ ID NO:28). The boxes show the randomized positions in the initial pools. Upper and lower rows show clones originated from pools 1 and 2, respectively.

Selection. These two pools were mixed and applied to selection with Biotin-Phe-CME as a substrate using the same procedures as previously reported. Activity became apparent after four rounds of selection (FIG. 2C), and the selection was continued two more rounds at a shorter incubation time (30 min→10 min) to enrich more active population. After cloning of the active population, 18 clones were arbitrarily chosen to test their self-aminoacylation activity and 16 active clones were identified. These clones were sequenced and aligned to classify the families (FIG. 3). We found that only two clones were originated from pool 1, and the remaining 14 clones were from pool 2, suggesting that active sequences are more abundant in pool 2. Between the two active clones in pool 1, the wild type sequence was partially recovered in the 12-19 random region. The bases that were not conserved are UU bulge, giving AC or UCA (U was inserted). U14 was not also recovered but mutated to C in both clones, and thus the size of bulge increased to 3 or 4 nucleotides. On the other hand, the remaining C15-A19 were wild type sequence, indicating the importance of this particular sequence for activity. In contrast, it was unexpected to find that the 46-56 random region did not yield either wild type or similar sequence between the two clones.

Between 14 clones isolated from pool 2, we found that the 36-39 random region completely became the wild type sequence. This strongly argues that this particular sequence is essential for activity. In contrast, the 46-56 region had neither wild type nor consensus sequence. This was consistent with the observation in the selected clones from pool 1 and indicated the importance of the 46-56 region in forming not only the P3 stem but also any structures.

Engineering truncated ribozymes. To confirm the above, we first constructed a truncated ribozyme based on the consensus sequence found in pool 2 where the entire sequence in the downstream of the tRNA binding site (beyond U45) was deleted. This truncated ribozyme showed virtually identical activity to clones isolated in pool 2 (data not shown). This ribozyme was further truncated by shortening the P1 stem like r24mini. Thus, a series of mutants (Fx series in FIG. 4A) varying the length of the complementary sequence to the $tRNA^{Asn}_{CCCG}$ 3'-end was constructed. In this series of mutants, the strength of the base pair interaction between the ribozyme and tRNA was tested.

The initial rates of the formation of aminoacyl-$tRNA^{Asn}_{CCCG}$ were analyzed for all constructs by streptavidin(SAv)-dependent gel-shift assay (FIG. 4B). Fx3 ribozyme that has a 3-base complementary sequence (G43-U45) to the tRNA 3'-end ($A_{73}$-$C_{75}$) exhibited the highest activity among the mutants tested (FIG. 4B). The observed rate of Fx3 ribozyme was 0.069 µM/min, which gave 29-fold higher activity than r24mini (0.0024 µM/min). Shortening the complementary bases to 2 (Fx2 ribozyme) reduced the observed rate significantly (0.0058 µM/min), indicating the necessity of the 3-base pairing interaction. On the other hand, increasing the complementary bases to 4 (Fx4 ribozyme) afforded mild reduction of activity (0.052 µM/min), whereas that to 5 (Fx5 ribozyme) decreased the observed rate further (0.021 µM/min). These results suggest that extension of the base pairing interaction between the ribozyme 3'-end and the tRNA acceptor stem does not contribute to increasing in activity, most likely because the bases added to the 3'-end of ribozyme cannot effectively invade the tRNA acceptor stem. It rather appears to act as a negative factor to interfere the essential base pair interaction of G43-U45 with $A_{73}$-$C_{75}$.

We also analyzed the end point of aminoacyl-tRNA product. The Fx3 ribozyme and Fx4 ribozyme construct gave the same end point. Although we could not actually observe the end points for Fx2 ribozyme and Fx5 ribozyme in a 90 min incubation due to the slow rate, their end points could be extrapolated to nearly the same end point as the other constructs. This suggests that the observed initial rates of the tRNA aminoacylation shown in FIG. 4B likely reflect the activity of each construct. We could not see greater than 50% of aminoacyl-tRNA in any experiments when $tRNA^{Asn}_{CCCG}$ was the substrate. This is because the active fraction of $tRNA^{Asn}_{CCCG}$ for accepting the aminoacyl group is less than 50% due to the heterogeneity of 3'-end and misfolding of the tRNA structure. This was supported by the observation that when different tRNAs were used, the end points were varied depending upon tRNA (data not shown).

Figure 5A:
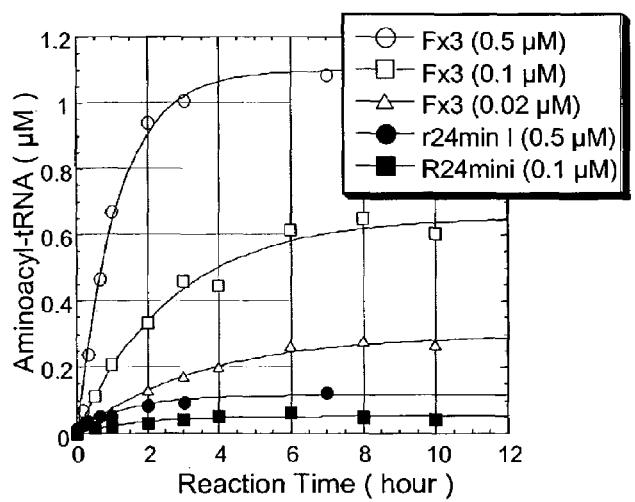
FIG. 5A shows comparison of the activities of various ribozymes and r24mini under multiple turnover conditions.
Figure 5B:
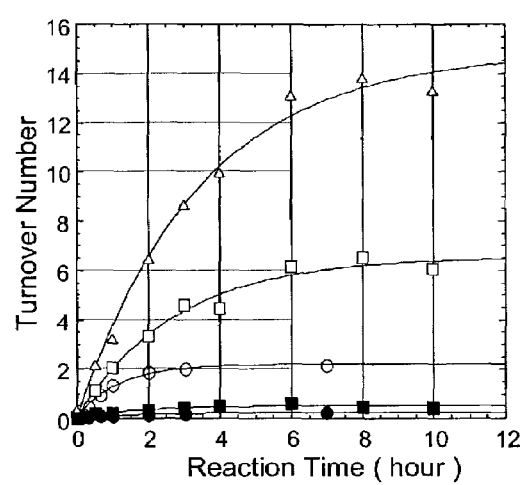
FIG. 5B. Turnover numbers of ribozyme. The concentrations of aminoacyl-tRNA observed in FIG. 5A were divided by each ribozyme concentration to determine the turnover numbers. Reactions were carried out in presence of 5 μM tRNA (tRNA$^{Asn}_{CCCG}$) for Fx3 ribozyme, v1-tRNA and r24mini, and 0.02, 0.1, or 0.5 μM Fx3 ribozyme or 0.5 or 0.1 μM r24mini, and incubated with 5 mM Biotin-Phe-CME at 25° C. Amounts of the aminoacyl-tRNA product were determined by streptavidin gel shift assay.

Multiple turnover ability. Having the optimized ribozyme for aminoacylation of $tRNA^{Asn}_{CCCG}$, multiple turnover activity of the Fx3 ribozyme was determined. In this series of experiments, we used a constant tRNA concentration at 5 µM and three concentrations of Fx3 ribozyme at 0.02, 0.1 and 0.5 µM. As expected, the apparent rate was faster when the higher concentration of Fx3 ribozyme was used (FIG. 5A), but the higher turnover number is observed at the lower concentration of Fx3 ribozyme (FIG. 5B). Thus, 0.02 µM Fx3 ribozyme displayed 14 turnovers, whereas 0.1 and 0.5 µM Fx3 ribozyme showed only 6 and 2 turnovers, respectively. It should be noted that the yield of aminoacyl-tRNA plateaud after the formation of 1 µM of aminoacyl-tRNA when 0.5 µµM Fx3 ribozyme was used. Because the reaction was completed within 2 h, hydrolysis of the substrate is negligible. This suggests that the turnover is inhibited by the aminoacyl-tRNA product. In contrast to the observation for Fx3 ribozyme, r24mini completely lacks multiple turnover ability (FIGS. 5A and B).

Aminoacylation of various tRNAs. To test if the Fx3 ribozyme is able to aminoacylate various tRNAs, we prepared two naturally occurring tRNAs ($tRNA^{fMet}$ and $tRNA^{Phe}$), three distinct non-natural tRNAs (otRNA, and v1-tRNA, and $tRNA^{Asn}_{CCCG}$). We also prepared three $tRNA^{Asn}_{CCCG}$ mutants containing different bases at position 73 ($N_{73}$, discriminator base) to determine the importance of recognition of this base by 45U in Fx3 ribozyme.

Figure 6A:
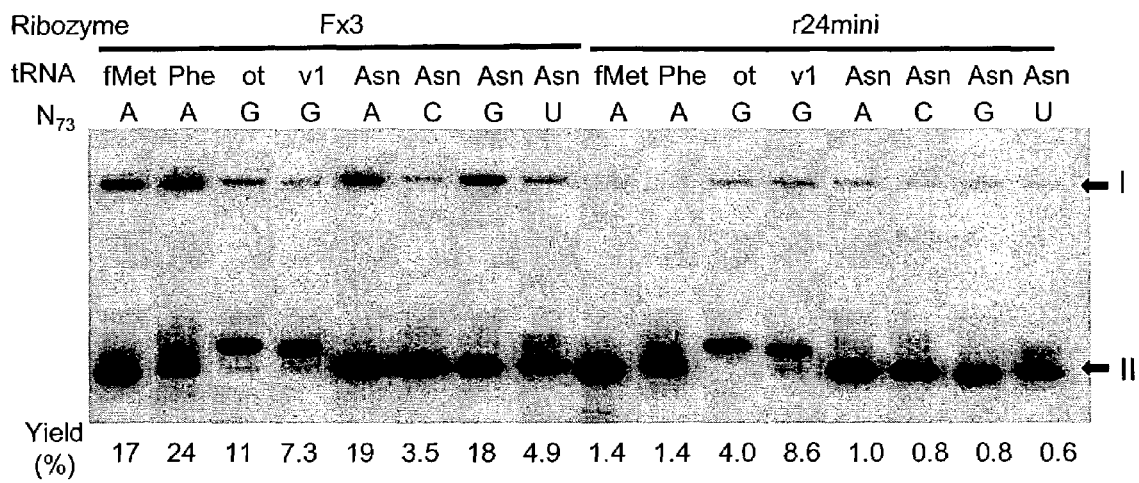
FIG. 6A shows aminoacylation activities Fx3 ribozyme and r24mini toward various tRNAs. Reactions were carried out in the presence of 1 μM tRNA and 2 μM Fx3 ribozyme or r24mini and incubated with 5 mM Biotin-Phe-CME at 25° C. for 3 min. Abbreviations: fMet, tRNA$^{f\text{-}Met}$; Phe, tRNA$^{Phe}$; v1, v1-tRNA; ot, otRNA; Asn, tRNA$^{Asn}$; $N_{73}$, discriminator base of tRNA; I, aminoacyl-tRNA complexed with streptavidin; II, unreacted tRNA.
Figure 6B:
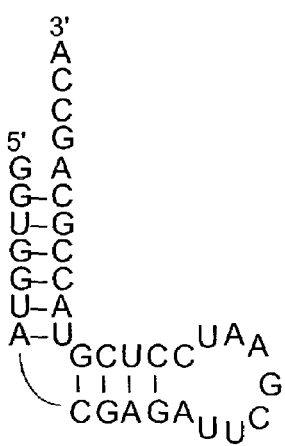
FIG. 6B shows secondary structure of the minihelix RNA (SEQ ID NO:49) derived from v1-tRNA.

We investigated the aminoacylation yield of each tRNA at 3 min incubation, which reflected the initial rate for the tRNA (FIG. 6A). The two natural tRNAs, $tRNA^{Asn(A)}_{CCCG}$, and $tRNA^{Asn(G)}_{CCCG}$, all of which have A or G of the discriminator base, were aminoacylated with comparable initial rates by Fx3 ribozyme. On the other hand, tRNA$^{Asn(C)}_{CCCG}$ and tRNA$^{Asn(U)}_{CCCG}$, both of which form a mispair with 45U in Fx3 ribozyme, were not aminoacylated as fast as the other tRNAs. In particular, tRNA$^{Asn(C)}_{CCCG}$ was aminoacylated more than 5-fold slower than tRNA$^{Asn(A)}_{CCCG}$. These results suggest that the difference in activities of the tRNA$^{Asn}_{CCCG}$ mutants is attributed to the recognition of the discriminator base by Fx3 ribozyme, which most likely reflects the increase in $K_M$ for the mispairing tRNAs.

In contrast, r24mini aminoacylates tRNAs with much poorer rates than Fx3 ribozyme (FIG. 6A). The yields of most tRNAs were less than 2%, and the only tRNA that showed a slightly higher yield (9%) was v1-tRNA. Thus, loss of such specific interactions in Fx3 ribozyme made it a better catalyst.

Figure 6C:
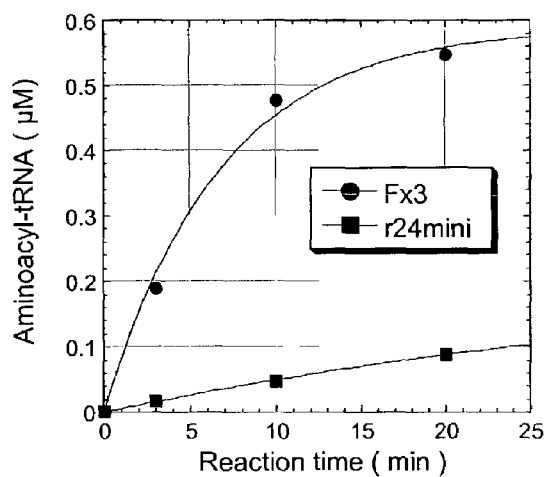
FIG. 6C shows comparison of aminoacylation activities of Fx3 ribozyme and r24mini. Reactions were carried out in presence of 1 μM minihelix RNA and 2 μM Fx3 ribozyme or r24mini, and incubated with 5 mM Biotin-Phe-CME at 25° C. I indicates aminoacyl-RNA complexed with streptavidin; II indicates unreacted minihelix RNA.
Figure 7A:
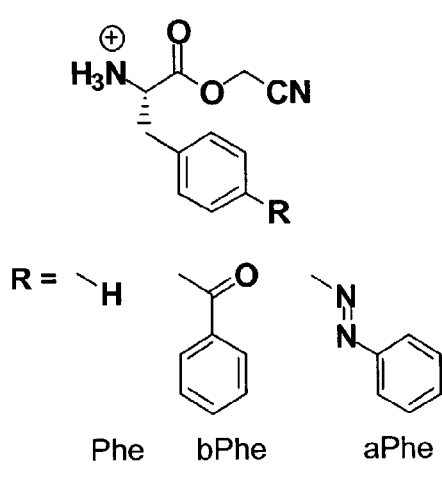
FIG. 7A shows Chemical structure of Phe and its analogs activated by cyanomethyl ester. Abbreviations: Phe, phenylalanine; bPhe, p-benzoyl-phenylalanine; aPhe, p-azophenyl-phenylalanine.

The above observation led us to test a simpler tRNA, minihelix RNA (FIG. 6A), as a substrate for aminoacylation by Fx3 ribozyme. Our previous studies on r24mini revealed that it could aminoacylate a minihelix RNA consisting of the acceptor and T stems of v1-tRNA but the activity is poorer than v1-tRNA. Fx3 ribozyme aminoacylates the minihelix RNA with a comparable rate to tRNA$^{Asn}_{CCCG}$ (FIG. 6C). We also observed that the end point was slightly increased compared with tRNA$^{Asn}_{CCCG}$, presumably due to its increased fraction of aminoacyl-accepting activity.

tRNA aminoacylation with non-natural amino acids. to compare the Fx3 ribozyme with r24mini, we chose two Phe analogs, p-benzoyl-phenylalanine (bphe) and p-azophenyl-phenylalanine (aPhe), both of which have a large group at the para substitution of the aromatic side chain (FIG. 7A). The side chains in the former and latter amino acids are photo-crosslinkable and photo-switchable groups.

Figure 7B:
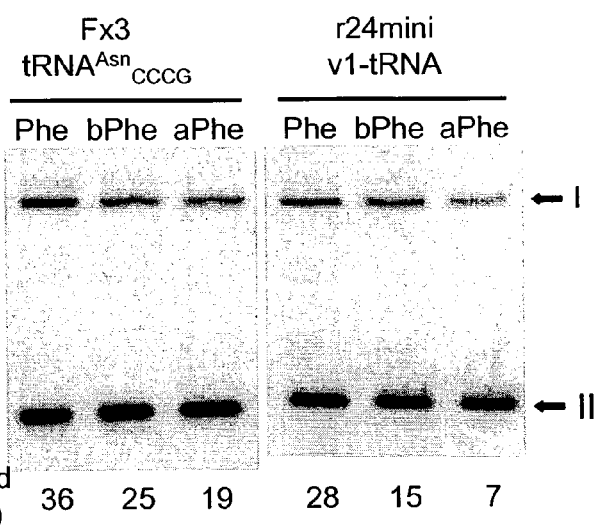
FIG. 7B shows a comparison of aminoacylation efficiencies of Fx3 ribozyme and r24mini with Phe analogs. Reactions were carried out in presence of 1 μM tRNA and 2 μM Fx3 ribozyme or r24mini, and incubated with 10 mM Phe or Phe analogs on ice for 2 hours. Note that because of instability of the α-NH$_2$ Phe substrates against hydrolysis, the reactions were carried out on ice instead of 25° C. To separate the aminoacyl-tRNA from unreacted tRNA, post-biotinylation of the product using biotin sulfo-NHS ester was performed in order to run the SAv-dependent gel shift assay. This method was previously known to selectively biotinylate the α-NH2 group. Abbreviations are the same as FIGS. 6A-6C.

As shown in FIG. 7B, Fx3 ribozyme exhibits greater activities toward both Phe analogs than r24mini. We have already confirmed the orthogonality of tRNA$^{Asn}_{CCCG}$ (that is inert to E. coli endogenous ARSs) and effective suppression of the programmed frame shift mutation on mRNA using a cell free translation system, so that the ability of Fx3 ribozyme to charge tRNA$^{Asn}_{CCCG}$ with the Phe analogs provides a new tool for non-natural amino acid incorporation into proteins.

EXAMPLE 2

Figure 8A:
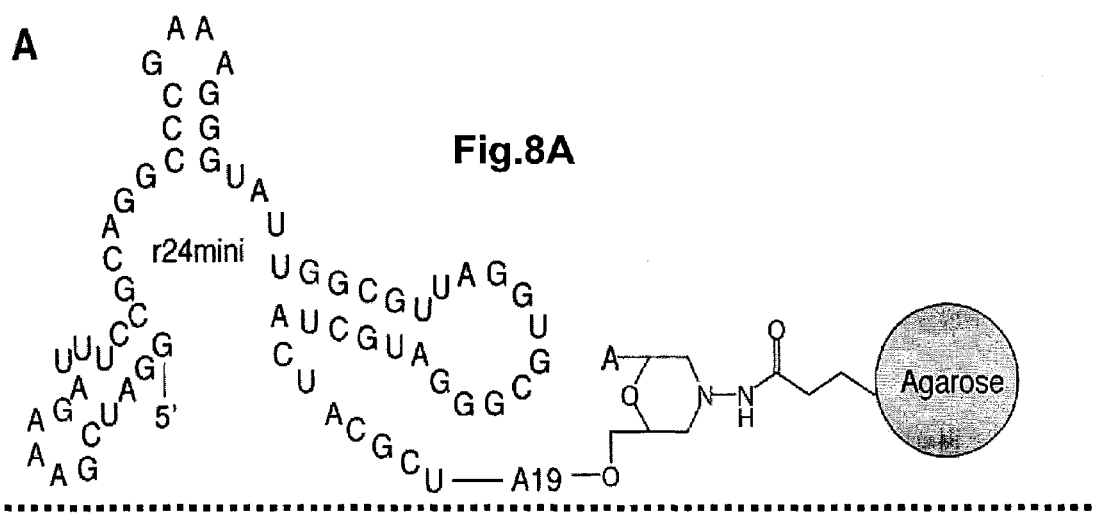
FIG. 8A shows secondary structure of the r24mini-A20 (SEQ ID NO:58) immobilized on an adipic acid dihydrazide resin. 20 adenosines were added at 3'-end of the wild type r24mini.
Figure 9A:
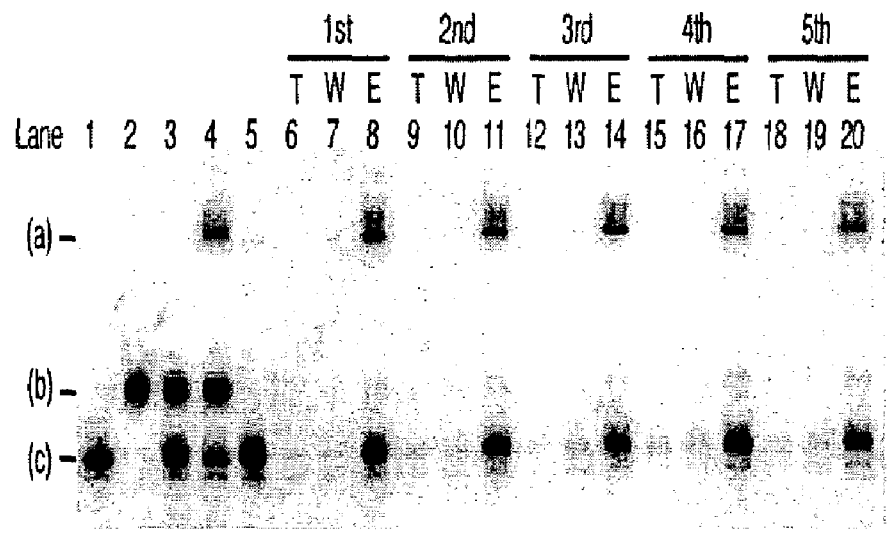
FIG. 9A shows an autoradiogram of the fractions isolated by the on-resin reaction. Both v1-tRNA and r24mini were internally radio-labeled with $^{32}$P. The aminoacylated v1-tRNAs were resolved by streptavidin-dependent gel mobility-shift assay. Reactions were carried out in presence of 10 μM v1-tRNA and 5 mM α-Biotin-Phe-CME (1) for 30 min at 37° C. Lanes 1, v1-tRNA ; 2, r24mini-A20; 3, reaction in solution in the absence of streptavidin; 4, the fraction in lane 3 in the presence streptavidin; 5, background reaction without r24mini ; 6-20; on-column reaction. T, fraction of wash through with the reaction buffer; W, fraction of wash through with a buffer containing 0.1 M NaOAc, 300 mM NaCl; E, fraction of elution with a buffer 0.1 M NaOAc, 300 mM NaCl, 7.5 M urea. (a) α-Biotin-Phe-tRNA complexed with streptavidin, (b) r24mini-A20, (c) tRNA.

Immobilizing a ribozyme on a resin is further demonstrated herein using the r24mini as an example of immobilization of any ribozyme on a resin, which is accomplished by taking advantage of the chemical structure of RNA. Periodate oxidation of the 3'-cis-diol on the ribose of RNA yields the corresponding dialdehyde. This functional group allows the immobilization of the RNA on an inexpensive hydrazide resin, and reductive amination makes the interaction an irreversible linkage. (FIG. 8A). To avoid compromising the ribozyme's integrity and activity due to perturbation of the requisite catalytic fold by the resin surface, the r24mini was engineered to bear an additional 20-nt adenosine linker at its 3'-end (r24miniA20 (SEQ ID NO:46); FIG. 8A). This modification did not affect on the catalytic ability in solution (FIG. 9A, lane 4). Thus, this engineered r24mini ribozyme was readily immobilized on the hydrazide resin at the designated site of the ribozyme.

Figure 9B:
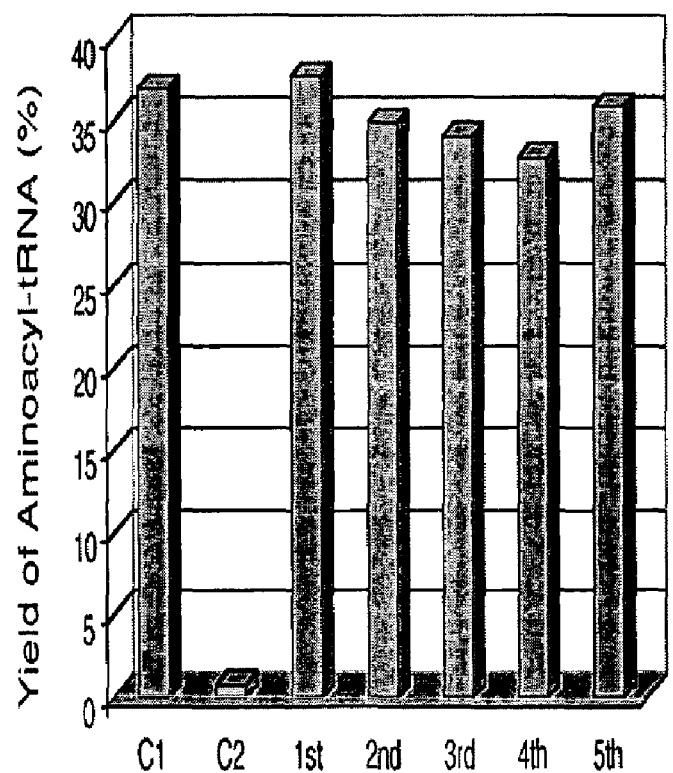
FIG. 9B shows aminoacylation efficiency determined by the streptavidin-dependent gel mobility-shift assay of the E fraction (E as in FIG. 9A) of each round. C1 and C2 indicate the yields of aminoacyl-tRNA in solution in the presence and absence of ribozyme, respectively.

The resin derivatized with r24mini-A20 was packed in a disposable column and then incubated with v1-tRNA to form the ribozyme-tRNA complex. The reaction was initiated upon the addition of the substrate 1 (FIG. 8A). After 30 minutes, the resin was washed with a sodium acetate buffer to remove the unreacted substrate and a trace amount of unbound v1-tRNA (FIG. 9A, lanes 6 and 7). Finally, the α-Biotin-Phe-tRNA along with unreacted tRNA was eluted from the resin using a urea buffer (lane 8). The yield of the aminoacyl-tRNA observed for the on-column reaction was 36%, which was comparable to that observed for the solution phase reaction (FIG. 9A, lanes 8 vs. 4; FIG. 9B, columns 1st vs. C1). In contrast, the background reaction in the absence of ribozyme was negligible (FIG. 9A, lane 5; FIG. 9B, column C2). The aminoacyl-tRNA fraction was not contaminated with ribozyme that had leached from the resin, suggesting that the ribozyme-resin was still intact after the washing-elution cycle.

After equilibration of the column with the reaction buffer, five additional rounds of on-column aminoacylation were carried out. We observed that the aminoacylation efficiency of the on-column reaction changed only nominally between cycles (FIG. 9A, lanes 9-20). This result demonstrates the durability and 'recyclability' of the ribozyme-resin. This allows for the rapid and easy isolation of aminoacyl-tRNA from the amino acid substrate and ribozyme.

Figure 8B:
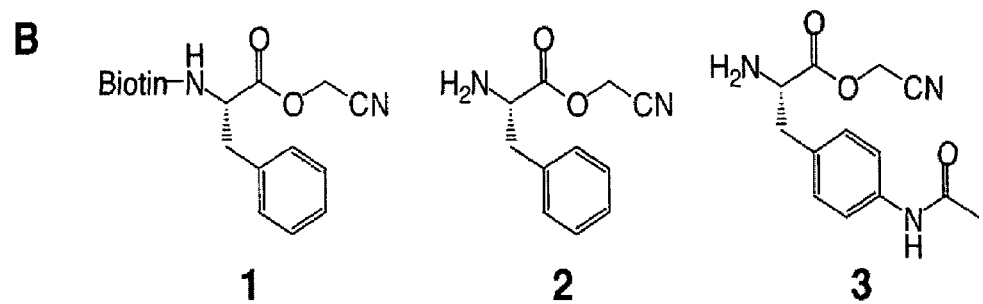
FIG. 8B shows amino acid substrates; 1 α-N-Biotinyl-L-phenylalanine cyanomethyl ester (α-Biotin-Phe-CME), 2 L-phenylalanine cyanomethyl ester (Phe-CME), 3 p-N-acetylamido-L-phenylalanine cyanomethyl ester (p-acetylamido-Phe-CME).
Figure 10:
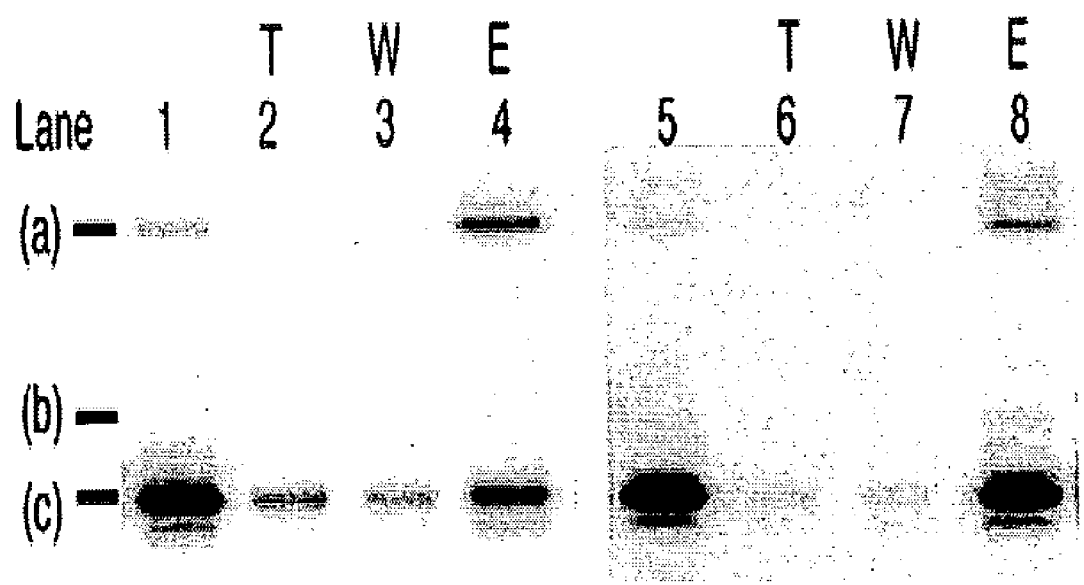
FIG. 10 shows on-column reaction of v1-tRNA with 2 (lanes 1-4) and 3 (lanes 5-8). Reactions were carried out in presence of 20 mM amino acid substrate for 5 min at 37° C. Lanes 1 and 5, background reaction without r24mini-A20 (SEQ ID NO: in solution; lanes 2-4 and 6-7, fractions isolated by the on-column reaction. T, W, E, and (a)-(c) are the same as those in FIG. 9A. In these assays, post-biotinylation was used to generate the corresponding Biotin-aminoacyl-tRNA, and the product was analyzed by streptavidin-dependent gel mobility-shift assay.

The aminoacylation of v1-tRNA took place on the resin after only a 5 minute incubation (FIG. 10, lane 4). Again, a 28% yield observed for this on-column aminoacylation is comparable to that for the solution phase (data not shown) and much greater than that observed for the background (FIG. 10, lane 1). We further examined the on-column aminoacylation reaction using a phenylalanine analog, p-acetylamido-Phe-CME as a non-natural amino acid (FIG. 8B, 3). The on-column aminoacylation reaction with this non-natural amino acid is shown to proceed, but with a yield lower than those observed for the other substrates tested in this study. This modest yield is due to the insufficient activity of r24mini-A20 toward 3, which was confirmed by the solution phase reaction. However, this is an expected outcome because this ribozyme was evolved with 1, and it shows remarkable specificity toward the natural side chain of Phe. This shortcoming of the r24mini has been overcome with the ribozyme of the present invention which can be affixed to the column as follows and catalyze aminoacylations as described in Example 1 above.

As a further example of attaching a ribozyme to a substrate, resin-immobilized Fx3 ribozyme is prepared by adding freshly prepared 0.1 M NaIO4 (400 μL) to 28.1 μM ribozyme (1 mL), and incubating the mixture at 0° C. for 20 min. The 3'-oxidized RNA is precipitated with 14 mL of 2% lithium perchlorate in acetone followed by washing with 1 mL of acetone. The pellet is dissolved in 1.4 mL of 0.1 M sodium acetate pH 5.0, and then mixed with adipic acid dihydrazide-agarose (resin:water=1:1 suspension 1.4 mL, washed by DEPC-treated water). The reaction solution is mixed at room temperature for 3 h. The resulting imine moiety of the RNA-resin is reduced by adding 1 M NaCNBH3 (300 μL), and then incubated at room temperature for 30 min. The agarose is washed by 1.4 mL of solution W1 (0.1 M Sodium acetate buffer pH 5.0 containing 300 mM NaCl, 7.5 M urea, 0.01% SDS) and suspended with 2 mL of solution W1 (the resulting volume was 2.8 mL). The ribozyme-resin can be stored in 4° C. for months. For immobilization to a solid support, such as a resin, the ribozyme may have a plurality of poly-adenosines on its 3' end. As an example not meant to be limiting in any way the poly-adenosine sequences may vary from 10 to 20 bases long. Representative examples of 20 adenosines at the 3' end of each ribozyme sequence are given for Fx2-A20 ribozyme (SEQ ID NO:33), Fx3-A20 (SEQ ID NO:34), Fx4-A20 ribozyme (SEQ ID NO:35) and Fx5-A20 (SEQ ID NO:36).

EXAMPLE 3

The following embodiment demonstrates the synthesis of a polypeptide having at least one desired amino acid at a selected position.

Methods

Preparation of ribozymes and tRNAs. The following polynucleotides were chemically synthesized and purified by 6% denaturing PAGE: Fx (5'-ACCTAACGCC AATACCCTT TCGGGCCTGC GGAAATCTTT CGATCC-3') (SEQ ID NO:38), P5-1 (5'-ACGCATATGT AATACGACTC ACTAT-AGGAT CGAAAGATTT CCGC-3')(SEQ ID NO:39), P5-2 (5'-GGTAACACGC ATATGTAATA CGACTC-3')(SEQ ID NO:40), P3-1 (5'-T20 ACCTAACGCC AATACCCTTT-3') (SEQ ID NO:41), P3-2 (5'-T20 ACCTAACGCC -3')(SEQ ID NO:42), P5-3 (5'-ACGCATATGT AATACGACTC ACTAT-AGCCT CTGTAGTTCAG TCGGT-3')(SEQ ID NO:43), P3-3 (5'-TGGTGCCTCT GACTGGACTC-3')(SEQ ID NO:44), tR (5'-TGGTGCCTCT GACTGGACTC GAAC-CAGTGA CATACGGATT XXXAGTCCGC CGTTC-TACCG ACTGAACTAC AGAGGC-3', XXX=TAG )(SEQ ID NO:45) or GGGT (SEQ ID NO:60).

The template DNA encoding the ribozyme sequences was amplified by PCR using the corresponding 5'- and 3'-primers (P5-1 and P3-1), and the resulting dsDNA was further amplified using shorter primers (P5-2 and P3-2). The template DNA (tR) coding the engineered tRNAAsn was amplified by PCR using the corresponding 5'- and 3' primers (P5-3 and P3-3), and the resulting dsDNA further amplified using shorter primers (P5-2 and P3-3). The Fx dsDNA or tR dsDNA was in vitro transcribed in the presence of 7.5 mM GMP, 3.75 mM each NTPs, and the RNA transcript was purified by 6% denaturing PAGE. For aminoacylation assay, the body-radiolabeled tRNA was synthesized by using the same protocol except for the presence of [α-32P]GTP in the transcription reaction.

Amino acids. Phe-CME (phenylalanine cyanomethyl ester), BezPhe-CME (p-benzoylphenyalanine cyanomethyl ester), and AzoPhe-CME (p-phenylazophenyalanine cyanomethyl ester) were synthesized using the same procedure as previously described (Goodman et al., JACS Vol 88, 21 Nov. 5, 1966. pp 5010-15.) IodPhe-CME (p-iodophenyalanine cyanomethyl ester), BiPhe-CME (p-biphenyalanine cyanomethyl ester), AzPhe-CME (p-azidophenyalanine cyanomethyl ester), and AcPhe (p-acetylphenyalanine cyanomethyl ester) were synthesized from the corresponding N-Boc amino acids by using same procedure as Phe-CME (Saito et al., EMBO J. 2001 Apr. 2; 20(7):1797-806). BioPhe (p-biotinyl-aminophenylalanine) was synthesized from N-Boc-p-aminophenylalanine and biotin-NHS. BioPhe-CME was synthesized using same procedure as Phe-CME. (Saito et al., EMBO J. 2001 Apr. 2; 20(7):1797-806).

Solution- and solid-phase aminoacylation. The solution-phase aminoacylations are carried out under the following conditions: 10 mM amino acid substrates (except that 5 mM Phe-CME and IodPhe-CME are used, and in the case of BiPhe-CME and AzoPhe-CME ethanol is added to the 5% final concentration in order to avoid its precipitation), 10 μM tRNA, 20 μM ribozyme in EK buffer [50 mM N-(2-hydroxyethyl)piperazine-N'-(3-propanesulfonic acid); EPPS, 12.5 mM KCl] buffer (pH 7.0), and 1.2 M MgCl2.

The solid-phase aminoacylation procedure is as follows: The tRNA is heated at 95° C. for 3 min and cooled to 25° C. over 5 min. This tRNA solution is mixed with the ribozyme-resin (5 μμL resin:water=1:3 suspension, washed by DEPC-treated water) followed by the addition of 4.5 M MgCl2. The 0.1 M amino acid substrate is added to the reaction mixture and pH is adjusted to 7 by the addition of an appropriate amount of 0.25 M KOH (generally an equal volume to the amino acid substrate solution was used). After 2 h incubation on ice, the supernatant is removed. The resin is washed with 20 μL of EK buffer (pH 7.5) containing 10 mM EDTA to elute the aminoacyl-tRNA product. After ethanol precipitation, the pellet is dissolved in 2.5 μL of EPPS (0.1 M, pH 5.9) containing 20 mM biotin-3-sulfo-N-hydroxylsuccinimide ester, and after cooling on ice the reaction is initiated by the addition of 0.86 μL of EPPS-KOH (0.3 M, pH 9.1, which brings the pH to about 8.0). After 1 h, the reaction is terminated by ethanol precipitation. The pellet is washed by 70% ethanol and dissolved into 10 μL of water. A 1 μL portion of the RNA solution is mixed with 4 μL of the loading buffer (0.62 mg/mL streptavidin, 50 mM EDTA, 33 mM piperazine-N'N-bis-[2-ethanesulfonic acid] pH 6.1, 6 M urea, heated for 30 sec at 95° C., and then cooled to 25° C. This sample is analyzed by 6% denaturing PAGE, run in a cold room in order to keep the gel temperature below 20° C. Under these conditions, the streptavidin-biotin complex is stable enough to retard the aminoacyl-tRNA band, but the RNA structure is mostly denatured.

Plasmid construction. The GFPUV-coding region was obtained from pGFPUV (Clonetech®, Palo Alto, Calif.) and His-Tag sequence was added by PCR using 5'-CATATG-GCTA GCAAAGGAGA AGAACTTTTC ACTGG-3'(SEQ ID NO:47) and 5'-ATACTCAAGC TTAGTGGTGG TGGTGGTGGT GTTTGTAGAG CTCATCCATGC-3' (SEQ ID NO:48) as primers and cloned into NheI and HindIII site of pGEMEX-1 (Promega®). Mutation of G72T, C192A, C193A, G240T, G312T, and G684T by standard mutagenesis protocols. The mutations at C192A and T193A were introduced to enhance fluorescence spectrum at 488 nm, and those at G72T, G240T, G312T, and G684T were done to remove minor codons (CGG and GGG). After sequencing the mutant, a silent mutation at A486G was found.

Translation. The batch translation (2.5 μL) was done using Rapid Translation System (RTS-100, Roche) in the presence of $^{35}$S-Met. The reaction was prepared according to the manufacturer's protocol with minor modifications of conditions as follows: A half amount of the amino acid mix was used instead of the manufacturer suggested amount, and 30 μM (final concentration) suppresser tRNA or its corresponding tRNA charged with Phe or Phe analogs was added. Each aminoacyl-tRNA was synthesized by the protocol described in the solid-phase aminoacylation. For a control, Phe-tRNA containing pdC75 was prepared according the literature procedure. After 1 h incubation at 30* C., the translation results were analyzed by 15% SDS-PAGE. Fluorescent activity of GFP was also analyzed by Molecular Imager FX. Prior to this analysis, 2 μL of 0.1 M Tris-HCl (pH 8.8) was added to 1 μL of the translation mixture, and kept at 4* C. overnight in order to generate the fluorescent active protein.

For MS spectrum analysis, the WT and mutant (Tyr 151 IodPhe) were translated in 110 μL scale under manufacturer's conditions containing 2 mM Met. The protein was then purified using TALON® (Clonetech®). Purity of the protein was conformed by 15% SDS-PAGE analysis followed by staining using GelCode® Blue Stain Reagent (PIRCE®). The protein concentration was also determined by Micro BCA Protein Assay Reagent using BSA as a standard (PIRCE®). The determined concentrations for wild type and mutant were 178

μg/mL and 76 μg/mL, respectively. These values correspond to the amounts isolated from 110 μL translation with 19.5 μg and 8.4 μg, respectively.

Post-translation modification. Mutant GFP (Tyr 151 AcPhe) and wild-type GFP labeled with $^{35}$S-Met were translated and purified using the same protocol as described above. 3 M sodium acetate (pH 5.0) was added to 10 μL of purified protein (what concentration?) and pH was adjusted to 5.0 by adding 2 M HCl. 3 μL of 0.1 M biotin-LC-hydrazide (PIRCE) in DMSO was added to the above protein solution, and incubated for 24 h. This solution was incubated with 0.75 μM of 1 M NaCNBH3 for 24 h to reduce the imine bond. To remove the excess amount of biotin-LC-hydrazide, the solution was first diluted with 200 μμL of 10 mM Tris-HCl (pH 8.8) and spun to remove any insoluble matters. The solution was then applied to BSA-precoated Microcon YM-10® (MILLIPORE®) and the remaining solution above the filter was collected. The collected protein was analyzed by streptavidin-gel-shift assay using 10% native PAGE. For the SAv-agarose capturing experiment, 5 μL of streptavidin-agarose (PIRCE®) was added to the protein and incubated for 10 min. The resulting mixture was diluted with 200 μL of 0.1 M Tris-HCl (pH 8.8), and fluorescent activity of the protein was analyzed by Molecular Imager FX®.

Results

FIGS. 12A-C demonstrate ribozyme-based aminoacylation of an engineered suppresser tRNA charged with phenylalanine and various non-natural amino acids. In FIG. 12A the cyanomethyl activated amino acids used in this example are shown with various groups at the p-position of phenyl ring represented by "R". The ribozymes of the present invention can tolerate a variety of substitutions at this position. Examples of non-natural amino acids shown in FIGS. 12 and 14 are phenylalanine, p-iodophenylalanine, p-benzoylphenylalanine, p-biphenylalanine, p-biotynyl-aminophenylalanine, p-azidophenylalanine, p-phenylazophenylalane. Further, the following non-natural amino acids can also be charged on tRNA and incorporated into a protein: p-hydroxyl-phenylalanine (tyrosine), tryptophane, 2-naphthylalanine, p-nitrophenylalanine, N-methyl-phenylalanine, 3-phenyl-2-hydroxylpropionic acid, and tetrahydroisoquinoline-3-carboxyacid.

In one embodiment, a ketone group is added at the R position shown in FIG. 12A. By adding the ketone group at this R position, a wide variety of post-translational modifications of the translated polypeptide are possible. Such modifications are well within the purview of those skilled in the art. By making post-translational modifications, such as the introduction of large R groups at the R positions shown in FIG. 12A via the ketone group, steric hindrances that would arise during translation because of these groups are avoided. This is because the ketone is a group to which an array of hydrazide molecules, including biotin, fluorescent molecules, molecules used in spin-labeling and many other examples can be selectively linked via a hydrazone bond. Moreover, this reversible covalent bond can be turned into an irreversible bond by the selective reduction of hydrazone by using a reducing agent, for example, sodium cyanoborohydride.

FIG. 12B depicts an aminoacylation analysis by a streptavidin(SAv)-dependent gel-shift assay. The amino acid specific biotinylation was done after an aminoacylation reaction to detect the aminoacyl-tRNAs. The presence of the shifted bands in the "+" lanes indicates the successful aminoacylation of the tRNA by the ribozyme. Data in FIG. 12C provides aminoacylation efficiencies corresponding to the gel shift data of FIG. 12B. The middle of the error bar represents the mean score from 3 different trials while the error bar represents a standard deviation of all trials. The abbreviations used in FIGS. 12B and C are as follows: (a), Aminoacyl-tRNA-streptavidin complex; (b), unaminoacylated tRNA; *, aminoacyl-tRNA containing dC75, which was prepared by the chemical aminoacylation method; **, tRNA that has a ACCC 4-base anticodon instead of CUA anticodon; Phe, phenylalanine; Iod, p-iodophenylalanine; Bzo, p-benzoylphenylalanine; BiPhe, p-biphenylalanine; Bio, p-biotynyl-aminophenylalanine; Az, p-azidophenylalanine; Azo, p-phenylazophenylalane.

Figure 13:
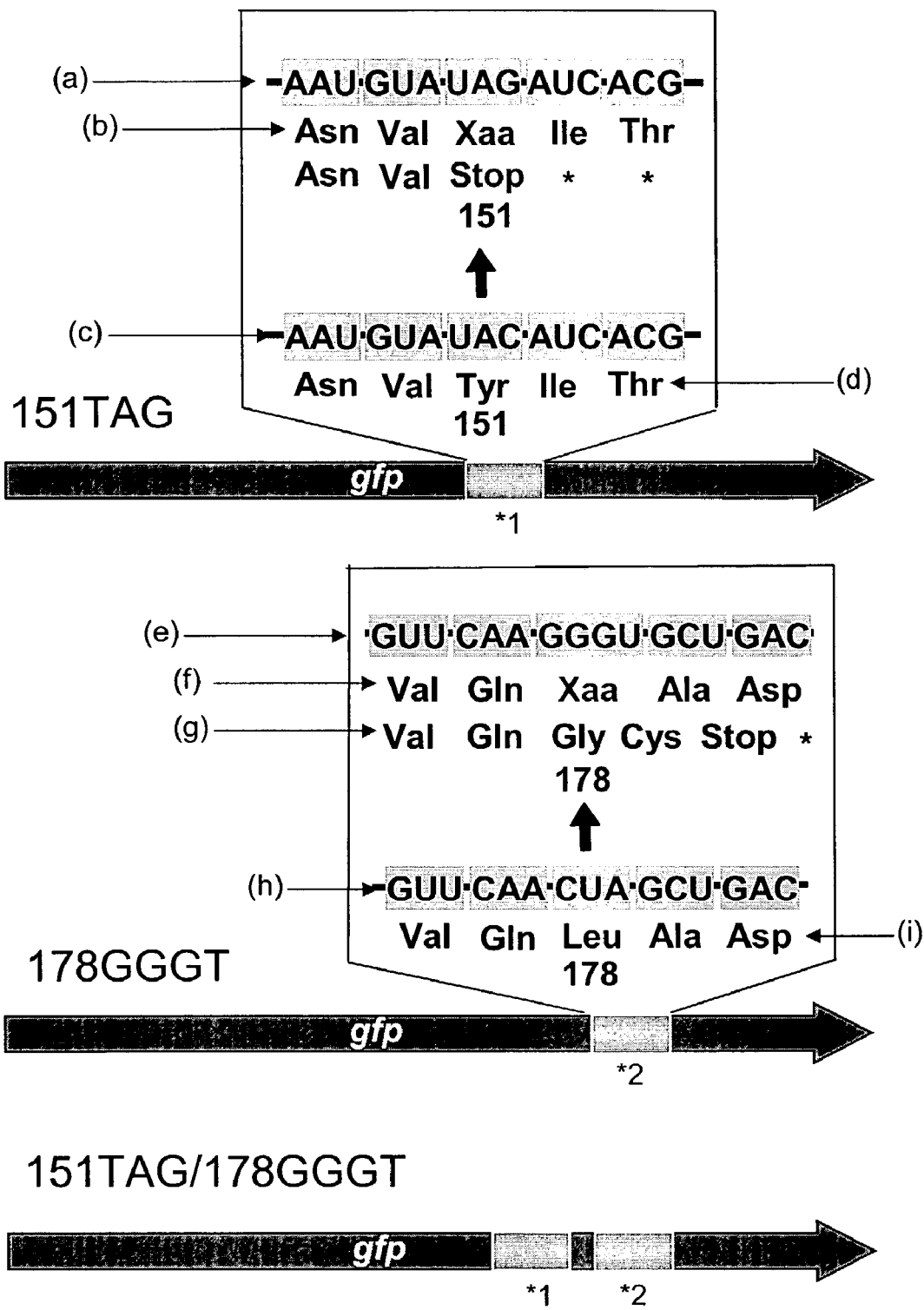
FIG. 13 shows examples of mutations of the Green Fluorescent Protein (GFP) gene used in this study. Amber (TAG) and 4-base (GGGT) codons were introduced at the designated positions for the incorporation of a single or multiple Phe analogs as shown for nucleotide and amino acid sequences (a) through (i). (a)(SEQ ID NO:51), (b)(SEQ ID NO:52), (c) (SEQ ID NO:53), (d)(SEQ ID NO:54), (e)(SEQ ID NO:55), (f)(SEQ ID NO:56), (g) (SEQ ID NO:57), (h)(SEQ ID NO:58), and (i)(SEQ ID NO:59).

FIG. 13. depicts mutant genes used in this Example. Amber (TAG) and 4-base (GGGT) codons were introduced at the designated positions for the incorporation of a single or multiple Phe analogs. The amino acids at 151 and 178 are present on the surface of GFP, which does not disturb protein folding.

mRNAs from the mutated gene obtained above (FIG. 13) were used for in vitro translations. FIGS. 14A-C provide data related to the non-natural amino acid mutagenesis of GFP at amino acid position 151 and make use of the following abbreviations: aa-tRNA, aminoacyl-tRNA; x, no tRNA; −, no aa-tRNA; +; aa-tRNA; (a), full-length protein; (b), truncated peptide. A band below (b) is an unknown truncated peptide, which exists in the translation for not only the mutant proteins but also wild type.

FIG. 14A depicts an SDS-PAGE analysis of translation reactions. The amber "TAG" mutation demonstrated in FIG. 13 was used in this experiment. Translation of mRNA with the TAG codon at 151 results in termination of translation at amino acid position 151 in GFP when a tRNA charged using a ribozyme of the present invention and bearing an anticodon complementary to the UAG codon at 151 is not present, as is shown in lane 3. Termination at 151 yields a peptide of about 17 kDa, while translating through the stop codon at 151 yields a polypeptide of about 30.6 kDa. Lane 1 includes the wild type mRNA without the 151 stop codon and results in the full-length GFP (the stop codon is replaced with UAC (see FIG. 13). From lane 2 through lane 11 the transcript with the 151 stop codon was used in the translation reactions. In lane 2, no suppressor tRNA was added and results in no full length product because the translational machinery cannot progress through the stop codon at 151. In lane 3, suppressor tRNA was added but with no charged amino acid; because the suppressor tRNA is orthogonal (inert) to the endogenous AARSs, the tRNA cannot be charged with natural amino acids, and thus this stop codon cannot be suppressed. In lane 4, a Phe-tRNA which was chemically synthesized using known, non-ribozyme based methods and containing dC75 was added to the translation reaction. In lanes 5-11, aminoacyl-tRNAs prepared by the ribozyme-resin were added to the translations, and the results demonstrate the feasibility of incorporating these amino acids using the methods of the present invention. The amino acids used are represented by the following abbreviations: Phe, phenylalanine; Iod, p-iodophenylalanine; Bzo, p-benzoylphenylalanine; BiPhe, p-biphenylalanine; Bio, p-biotynyl-aminophenylalanine; Az, p-azidophenylalanine; Azo, p-phenylazophenylalane.

In FIG. 14B, the fluorescence activity of each GFP synthesized with the conditions depicted in FIG. 14A is shown as analyzed by Molecular Imager FX. As can be seen, the incorporation of the non-natural amino acids does not eliminate the fluorescence of the GFP.

In FIG. 14C the "suppression efficiency" is shown. Suppression efficiency is a measure of how efficiently the 4-base codon mutation (178GGGT) on mRNA is suppressed by the aminoacyl-tRNA that has ACCC (aminoacyl-tRNA$_{ACCC}$) during the translation. The middle of the error bar represents the mean score form 3 different trials. The error bar represents a standard deviation of all trials.

The site-specific incorporation of two non-natural amino acids is demonstrated in FIGS. 15A-C.

In FIG. 15A an SDS-PAGE analysis of translation reaction is shown. The abbreviations are as follows: x, no tRNA; −, no aa-tRNA; +; aa-tRNA; (a), full-length protein; (b), truncated peptide at position 180 (failed frame shift); (c) truncated peptide at position 151 (amber stop codon). The lanes in FIG. 15A depict the following. Lane 1 shows a translation of wild type, full-length GFP as a positive control and size marker. Lane 2 shows translation of 151TAG mutant in the absence of both tRNACUA and tRNAACCC suppressor tRNAs. Lane 3 shows translation of 1the 51TAG mutant in the presence of tRNACUA, but without the phenylalanine analog Bip. This demonstrates the orthogonality of tRNACUA. Lane 4 shows translation of 151 TAG mutant in the presence of Bip-tRNACUA (aminoacylated tRNACUA). Lane 5 shows Translation of 178GGGT mutant in the absence of suppressor tRNAs. Lane 6 shows translation of 178GGGT mutant in the presence of tRNAACCC (but without the phenylalanine analog Ido). This indicates the orthogonality of tRNAACCC. Lane 7 shows translation of 178GGGT mutant in the presence of Ido-tRNAACCC. Lane 8 shows translation of double mutant, 151TAG/178GGGT, in the absence of suppressor tRNAs Lane 9 shows translation of 151TAG/178GGGT mutant in the presence of tRNACUA and tRNAACCC. Lane 10 shows translation of 15 1TAG/178GGGT mutant in the presence of Bip-tRNACUA. Lane 11 shows translation of 151TAG/178GGGT mutant in the presence of Ido-tRNAACCC. Lane 12 shows translation of 151TAG/178GGGT mutant in the presence of Bip-tRNACUA and Ido-tRNAACCC. Thus, the translation through 178GGGT and 151TAG/178GGGT as shown in lane 12 demonstrates the use of two different aminoacylated tRNAs charged by the ribozyme of the present invention for incorporation of non-natural amino acids into a polypeptide.

In FIG. 15B, the fluorescent activity of each GFP, analyzed by Molecular Imager FX is shown and demonstrates the fluorescent capacity of GFP with non-natural amino acids incorporated by the methods of the present invention.

In FIG. 15C the suppression efficiency of the tRNAs is shown. Suppression efficiency is a measure of how efficiently the amber mutation (I51 TAG) and 4-base codon mutation (178GGGT) on mRNA is suppressed by the corresponding aminoacyl-tRNAs that have CUA (aminoacyl-tRNA$_{CUA}$) and ACCC (aminoacyl-tRNA$_{ACCC}$) anticodons during the translation. The middle of the error bar represents the mean score form 3 different trials. The error bar represents a standard deviation of all trials.

The feasibility of post-translation modification of GFP after translation using the tRNAs aminoacylated with the ribozyme of the present invention is shown in FIGS. 16A-C. In FIG. 16A is shown a schematic representation of biotin-modification of GFP wherein AcPhe (p-acetylphenylalanine) was incorporated at position 151. The ribozyme-resin-catalyzing tRNA aminoacylation efficiency using the AcPhe substrate was 45% determined by SAv-dependent gel-shift assay, and the suppression efficiency was 40% determined by SDS-PAGE (data not shown). After protein purification, the keto group of 151AcPhe was modified by biotin-LC-hydrazide.

FIG. 16B depicts SAv-dependent gel-shift assay of wild type and biotinylated 151AcPhe mutant GFPs. Approximately 80% of the mutant GFP band was retarded by the addition of SAv, whereas no shift was observed for wild type. This confirms the specific biotin modification on the methyl ketone group of the phenylalanine analog at position 151.

In FIG. 16C the SAv-agarose (aga) capture of the mutant GFP in Eppendorf tubes is shown. SAv-agarose binding to the biotinylated mutant GFP successfully captured the GFP and concentrated it on the resin, whereas no capture was observed for wild type.

Thus, this invention demonstrates that multiple non-natural amino acid can be incorporated into a functional polypeptide at desired positions and post-translational modification of the polypeptide using the tRNAs aminoacylated with non-natural amino acids by a ribozyme.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A polynucleotide comprising a sequence encoding a ribozyme, said ribozyme being capable of aminoacylating a tRNA with a non-cognate amino acid, wherein the sequence encoding the ribozyme is selected from the group consisting of SEQ ID NO:29, SEQ ID NO:30, SEQ ID NO:31, and SEQ ID NO:32.

2. The polynucleotide of claim 1, wherein said non-cognate amino acid is selected from the group consisting of natural and non-natural amino acids.

3. The polynucleotide of claim 2, wherein said non-natural amino acid is selected from the group consisting of p-benzoylphenylalanine, p-azophenylphenylalanine, p-iodophenyalanine, p-biphenyalanine, p-azidophenyalanine, and p-phenylazophenylalane.

4. The polynucleotide of claim 1, wherein said non-cognate amino acid has a free α-amino group.

5. The polynucleotide of claim 1, wherein said non-cognate amino acid is capable of being incorporated into a polypeptide.

6. The polynucleotide of claim 1, wherein said tRNA has an anticodon corresponding to a stop codon.

7. The polynucleotide of claim 1, wherein said tRNA has an anticodon consisting of four nucleotides.

8. The polynucleotide of claim 1 wherein the ribozyme further comprises a plurality of adenosine residues at the 3' end.

9. The polynucleotide of claim 8 wherein the polynucleotide is immobilized on a solid substrate.

10. The polynucleotide of claim 7 wherein the solid substrate is selected from the group consisting of agarose, sepharose and magnetic beads.

11. A method of aminoacylating a tRNA with a non-cognate amino acid comprising the steps of:

a) providing a ribozyme capable of aminoacylating tRNA with a non-cognate amino acid; wherein the ribozyme has a nucleotide sequence selected from the group consisting of SEQ ID NO:29, SEQ ID NO:30, SEQ ID NO:31, and SEQ ID NO:32:
   i) preparing a mixture comprising;
b) providing a tRNA;
c) providing a non-cognate amino acid; and
d) combining a), b) and c) to effect aminoacylation of the tRNA with the non-cognate amino acid.

12. The method of claim 11, wherein the non-cognate amino acid is a non-natural amino acid.

13. The amino acid of claim 12 wherein the non-natural amino acid is selected from the group consisting of p-benzoylphenyalanine, p-azophenylphenylalanine, p-iodophenyalanine, p-biphenyalanine, p-azidophenylalanine, and p-phenylazophenylaline.

14. The method of claim 11 wherein the non-cognate amino acid has a free $\alpha$-amine.

15. The method of claim 11 wherein the non-cognate amino acid is capable of being incorporated into a polypeptide.

16. The method of claim 11 wherein the tRNA has an anticodon corresponding to a stop codon.

17. The method of claim 11 wherein the tRNA has an anticodon consisting of four nucleotides.

18. The method of claim 11 wherein the ribozyme is immobilized to a solid substrate.

19. The method of claim 18, wherein the ribozyme is immobilized to a solid substrate via a plurality of adenosine residues at the 3' end.

20. The method of claim 11, further comprising the step of isolating the aminoacylated tRNA from the ribozyme.

* * * * *

SEQUENCE LISTING

```
<160> NUMBER OF SEQ ID NOS: 61

<210> SEQ ID NO 1
<211> LENGTH: 57
<212> TYPE: RNA
<213> ORGANISM: artificial sequence
<220> FEATURE:
<221> NAME/KEY: misc_RNA
<222> LOCATION:
<223> OTHER INFORMATION: synthesized

<400> SEQUENCE: 1
ggaucgaaag auuuccgcag gcccgaaagg guauuggcgu uaggugcggg augcuac          57

<210> SEQ ID NO 2
<211> LENGTH: 76
<212> TYPE: RNA
<213> ORGANISM: artificial sequence
<220> FEATURE:
```

<223> OTHER INFORMATION: synthesized

<400> SEQUENCE: 2
ggugguaucc ccaaggggua agggaccgga uucccgaauc cggcauuccg agguucgaau    60
ccucguaccg cagcca                                                   76

<210> SEQ ID NO 3
<211> LENGTH: 74
<212> TYPE: RNA
<213> ORGANISM: artificial sequence
<220> FEATURE:
<221> NAME/KEY: misc_RNA
<222> LOCATION:
<223> OTHER INFORMATION: synthesized

<400> SEQUENCE: 3
ggugguaucc ccaagggguac gggaccggau ucccgaaucc ggcauucgag auucgaaucc   60
ucguaccgca gcca                                                     74

<210> SEQ ID NO 4
<211> LENGTH: 76
<212> TYPE: RNA
<213> ORGANISM: artificial sequence
<220> FEATURE:
<221> NAME/KEY: misc_RNA
<222> LOCATION:
<223> OTHER INFORMATION: synthesized

<400> SEQUENCE: 4
gccucuguag uucagucggu agaacggcga cucccgaauc cguaugucac ugguucgagu    60
ccagucagag gcacca                                                   76

<210> SEQ ID NO 5
<211> LENGTH: 76
<212> TYPE: RNA
<213> ORGANISM: artificial sequence
<220> FEATURE:
<221> NAME/KEY: unsure
<222> LOCATION: 21-28, 55-65
<223> OTHER INFORMATION: synthesized; n is u,c,a or g

<400> SEQUENCE: 5
ggaucgucag ugcauugaga nnnnnnnngg cccgaaaggg uauuggcguu aggunnnnn     60 nnnnncuacg cuaaaa                                                   76

<210> SEQ ID NO 6
<211> LENGTH: 76
<212> TYPE: RNA
<213> ORGANISM: artificial sequence
<220> FEATURE:
<221> NAME/KEY: unsure
<222> LOCATION: 41-44, 51-65
<223> OTHER INFORMATION: synthesized; n is u,c,a or g

<400> SEQUENCE: 6
ggaucgucag uugagauuuc cgcaggcccg aaacccuauu nnnnuuaggu nnnnnnnnn     60 nnnnncuacg cuaaaa                                                   76

<210> SEQ ID NO 7
<211> LENGTH: 97
<212> TYPE: DNA
<213> ORGANISM: artificial sequence
<220> FEATURE:
<221> NAME/KEY: unsure

```
<222> LOCATION: 21-28,55-65
<223> OTHER INFORMATION: synthesized; n is g, a, t or c

<400> SEQUENCE: 7
ggatcgtcag tgcattgaga nnnnnnnngg cccgaaaggg tattggcgtt aggtnnnnnn      60
nnnnnactac gctaaaagcc tctgtagttc agtcggt                              97

<210> SEQ ID NO 8
<211> LENGTH: 101
<212> TYPE: DNA
<213> ORGANISM: artificial sequence
<220> FEATURE:
<221> NAME/KEY: unsure
<222> LOCATION: 45-48, 55-69
<223> OTHER INFORMATION: synthesized; n is g, a, t or c

<400> SEQUENCE: 8
ggatcgtcag tgcattgaga tttccgcagg cccgaaaggg tattnnnntt aggtnnnnnn      60
nnnnnnnnna ctacgctaaa agcctctgta gttcagtcgg t                         101

<210> SEQ ID NO 9
<211> LENGTH: 52
<212> TYPE: DNA
<213> ORGANISM: artificial sequence
<220> FEATURE:
<223> OTHER INFORMATION: synthesized

<400> SEQUENCE: 9
ggtaacacgc atatgtaata cgactcacta ggatcgtc agtgcattga ga               52

<210> SEQ ID NO 10
<211> LENGTH: 77
<212> TYPE: DNA
<213> ORGANISM: artificial sequence
<220> FEATURE:
<223> OTHER INFORMATION: synthesized

<400> SEQUENCE: 10
tggtgcctct gactggactc gaaccagtga catacggatt cgggagtccg ccgttctacc      60
gactgaacta cagaggc                                                    77

<210> SEQ ID NO 11
<211> LENGTH: 20
<212> TYPE: DNA
<213> ORGANISM: artificial sequence
<220> FEATURE:
<223> OTHER INFORMATION: synthesized

<400> SEQUENCE: 11
tggtgcctct gactggactc                                                 20

<210> SEQ ID NO 12
<211> LENGTH: 56
<212> TYPE: DNA
<213> ORGANISM: artificial sequence
<220> FEATURE:
<223> OTHER INFORMATION: synthesized

<400> SEQUENCE: 12
tttccgcagg cccgaaaggg tattggcgtt aggtgcggga tgctactacg ctaaaa         56

<210> SEQ ID NO 13
<211> LENGTH: 56
<212> TYPE: DNA
```

```
<213> ORGANISM: artificial sequence
<220> FEATURE:
<223> OTHER INFORMATION: synthesized

<400> SEQUENCE: 13
accccgcagg cccgaaaggg tattggcgtt aggtgggagg taactctacg ctaaaa        56

<210> SEQ ID NO 14
<211> LENGTH: 57
<212> TYPE: DNA
<213> ORGANISM: artificial sequence
<220> FEATURE:
<223> OTHER INFORMATION: synthesized

<400> SEQUENCE: 14
tcacccgcag gcccgaaagg gtattggcgt taggtagccg acttgactac gctaaaa        57

<210> SEQ ID NO 15
<211> LENGTH: 60
<212> TYPE: DNA
<213> ORGANISM: artificial sequence
<220> FEATURE:
<223> OTHER INFORMATION: synthesized

<400> SEQUENCE: 15
tttccgcagg cccgaaaggg tattggcgtt aggtttgagc gggtctgaac tacgctaaaa     60

<210> SEQ ID NO 16
<211> LENGTH: 60
<212> TYPE: DNA
<213> ORGANISM: artificial sequence
<220> FEATURE:
<223> OTHER INFORMATION: synthesized

<400> SEQUENCE: 16
tttccgcagg cccgaaaggg tattggcgtt aggtgctcct agctttctac tacactaaaa     60

<210> SEQ ID NO 17
<211> LENGTH: 60
<212> TYPE: DNA
<213> ORGANISM: artificial sequence
<220> FEATURE:
<223> OTHER INFORMATION: synthesized

<400> SEQUENCE: 17
tttccgcagg cccgaaaggg tattggcgtt aggtgcatca cagggctttc tacgctaaaa     60

<210> SEQ ID NO 18
<211> LENGTH: 60
<212> TYPE: DNA
<213> ORGANISM: artificial sequence
<220> FEATURE:
<223> OTHER INFORMATION: synthesized

<400> SEQUENCE: 18
tttccgcagg cccgaaaggg tattggcgtt aggtaggccg tggcgggaac tacgctaaaa     60

<210> SEQ ID NO 19
<211> LENGTH: 60
<212> TYPE: DNA
<213> ORGANISM: artificial sequence
<220> FEATURE:
<223> OTHER INFORMATION: synthesized

<400> SEQUENCE: 19
tttccgcagg cccgaaaggg tattggcgtt aggtgaacgc gaaagaggac tacgctaaaa     60
```

<210> SEQ ID NO 20
<211> LENGTH: 60
<212> TYPE: DNA
<213> ORGANISM: artificial sequence
<220> FEATURE:
<223> OTHER INFORMATION: synthesized

<400> SEQUENCE: 20
tttccgcagg cccgaaaggg tattggcgtt aggtgcgata tccgattgcg tacgctaaaa      60

<210> SEQ ID NO 21
<211> LENGTH: 60
<212> TYPE: DNA
<213> ORGANISM: artificial sequence
<220> FEATURE:
<223> OTHER INFORMATION: synthesized

<400> SEQUENCE: 21
tttccgcagg cccgaaaggg tattggcgtt aggtaattaa gcgactcgcg tacgctaaaa      60

<210> SEQ ID NO 22
<211> LENGTH: 60
<212> TYPE: DNA
<213> ORGANISM: artificial sequence
<220> FEATURE:
<223> OTHER INFORMATION: synthesized

<400> SEQUENCE: 22
tttccgcagg cccgaaaggg tattggcgtt aggtacaaag gcgtccagcg tacgctaaaa      60

<210> SEQ ID NO 23
<211> LENGTH: 60
<212> TYPE: DNA
<213> ORGANISM: artificial sequence
<220> FEATURE:
<223> OTHER INFORMATION: synthesized

<400> SEQUENCE: 23
tttccgcagg cccgaaaggg tattggcgtt aggtgccgtt agttactgac tacgctaaaa      60

<210> SEQ ID NO 24
<211> LENGTH: 59
<212> TYPE: DNA
<213> ORGANISM: artificial sequence
<220> FEATURE:
<223> OTHER INFORMATION: synthesized

<400> SEQUENCE: 24
tttccgcagg cccgaaaggg tattggcgtt aggtgcaata gctatgaggc tagctaaaa       59

<210> SEQ ID NO 25
<211> LENGTH: 59
<212> TYPE: DNA
<213> ORGANISM: artificial sequence
<220> FEATURE:
<223> OTHER INFORMATION: synthesized

<400> SEQUENCE: 25
tttccgcagg cccgaaaggg tattggcgtt aggttagata gcaaataggc tcgctaaaa       59

<210> SEQ ID NO 26
<211> LENGTH: 59
<212> TYPE: DNA
<213> ORGANISM: artificial sequence
<220> FEATURE:

-continued

<223> OTHER INFORMATION: synthesized

<400> SEQUENCE: 26
tttccgcagg cccgaaaggg tattggcgtt aggtttgcag cacagtggct acgctaaaa      59

<210> SEQ ID NO 27
<211> LENGTH: 59
<212> TYPE: DNA
<213> ORGANISM: artificial sequence
<220> FEATURE:
<223> OTHER INFORMATION: synthesized

<400> SEQUENCE: 27
tttccgcagg cccgaaaggg tattggcgtt aggtgctgga gagttggact acgctaaaa      59

<210> SEQ ID NO 28
<211> LENGTH: 53
<212> TYPE: DNA
<213> ORGANISM: artificial sequence
<220> FEATURE:
<223> OTHER INFORMATION: synthesized

<400> SEQUENCE: 28
tttccgcagg cccgaaaggg tattggcgtt aggtgtttgg ctctacgcta aaa            53

<210> SEQ ID NO 29
<211> LENGTH: 44
<212> TYPE: RNA
<213> ORGANISM: artificial sequence
<220> FEATURE:
<223> OTHER INFORMATION: synthesized

<400> SEQUENCE: 29
ggaucgaaag auuccgcag gcccgaaagg guauuggcgu uagg                       44

<210> SEQ ID NO 30
<211> LENGTH: 45
<212> TYPE: RNA
<213> ORGANISM: artificial sequence
<220> FEATURE:
<223> OTHER INFORMATION: synthesized

<400> SEQUENCE: 30
ggaucgaaag auuccgcag gcccgaaagg guauuggcgu uaggu                      45

<210> SEQ ID NO 31
<211> LENGTH: 46
<212> TYPE: RNA
<213> ORGANISM: artificial sequence
<220> FEATURE:
<223> OTHER INFORMATION: synthesized

<400> SEQUENCE: 31
ggaucgaaag auuccgcag gcccgaaagg guauuggcgu uaggug                     46

<210> SEQ ID NO 32
<211> LENGTH: 47
<212> TYPE: RNA
<213> ORGANISM: artificial sequence
<220> FEATURE:
<223> OTHER INFORMATION: synthesized

<400> SEQUENCE: 32
ggaucgaaag auuccgcag gcccgaaagg guauuggcgu uaggugc                    47

```
<210> SEQ ID NO 33
<211> LENGTH: 64
<212> TYPE: RNA
<213> ORGANISM: artificial sequence
<220> FEATURE:
<223> OTHER INFORMATION: synthesized

<400> SEQUENCE: 33
ggaucgaaag auuuccgcag gcccgaaagg guauuggcgu uaggaaaaaa aaaaaaaaaa      60
aaaa                                                                  64

<210> SEQ ID NO 34
<211> LENGTH: 65
<212> TYPE: RNA
<213> ORGANISM: artificial sequence
<220> FEATURE:
<223> OTHER INFORMATION: synthesized

<400> SEQUENCE: 34
ggaucgaaag auuuccgcag gcccgaaagg guauuggcgu uagguaaaaa aaaaaaaaaa      60
aaaaa                                                                 65

<210> SEQ ID NO 35
<211> LENGTH: 66
<212> TYPE: RNA
<213> ORGANISM: artificial sequence
<220> FEATURE:
<223> OTHER INFORMATION: synthesized

<400> SEQUENCE: 35
ggaucgaaag auuuccgcag gcccgaaagg guauuggcgu uaggugaaaa aaaaaaaaaa      60
aaaaaa                                                                66

<210> SEQ ID NO 36
<211> LENGTH: 67
<212> TYPE: RNA
<213> ORGANISM: artificial sequence
<220> FEATURE:
<223> OTHER INFORMATION: synthesized

<400> SEQUENCE: 36
ggaucgaaag auuuccgcag gcccgaaagg guauuggcgu uaggugcaaa aaaaaaaaaa      60
aaaaaaa                                                               67

<210> SEQ ID NO 37
<211> LENGTH: 50
<212> TYPE: DNA
<213> ORGANISM: artificial sequence
<220> FEATURE:
<223> OTHER INFORMATION: synthesized

<400> SEQUENCE: 37
ggtaacacgc atatgtaata cgactcacta taggatcgaa agatttccgc                50

<210> SEQ ID NO 38
<211> LENGTH: 45
<212> TYPE: DNA
<213> ORGANISM: artificial sequence
<220> FEATURE:
<223> OTHER INFORMATION: synthesized

<400> SEQUENCE: 38
acctaacgcc aatacccttt cgggcctgcg gaaatctttc gatcc                     45
```

<210> SEQ ID NO 39
<211> LENGTH: 44
<212> TYPE: DNA
<213> ORGANISM: artificial sequence
<220> FEATURE:
<223> OTHER INFORMATION: synthesized

<400> SEQUENCE: 39
acgcatatgt aatacgactc actataggat cgaaagattt ccgc                    44

<210> SEQ ID NO 40
<211> LENGTH: 26
<212> TYPE: DNA
<213> ORGANISM: artificial sequence
<220> FEATURE:
<223> OTHER INFORMATION: synthesized

<400> SEQUENCE: 40
ggtaacacgc atatgtaata cgactc                                        26

<210> SEQ ID NO 41
<211> LENGTH: 40
<212> TYPE: DNA
<213> ORGANISM: artificial sequence
<220> FEATURE:
<223> OTHER INFORMATION: synthesized

<400> SEQUENCE: 41
tttttttttt tttttttttt acctaacgcc aataccettt                         40

<210> SEQ ID NO 42
<211> LENGTH: 30
<212> TYPE: DNA
<213> ORGANISM: artificial sequence
<220> FEATURE:
<223> OTHER INFORMATION: synthesized

<400> SEQUENCE: 42
tttttttttt tttttttttt acctaacgcc                                    30

<210> SEQ ID NO 43
<211> LENGTH: 46
<212> TYPE: DNA
<213> ORGANISM: artificial sequence
<220> FEATURE:
<223> OTHER INFORMATION: synthesized

<400> SEQUENCE: 43
acgcatatgt aatacgactc actatagcct ctgtagttca gtcggt                  46

<210> SEQ ID NO 44
<211> LENGTH: 20
<212> TYPE: DNA
<213> ORGANISM: artificial sequence
<220> FEATURE:
<223> OTHER INFORMATION: synthesized

<400> SEQUENCE: 44
tggtgcctct gactggactc                                               20

<210> SEQ ID NO 45
<211> LENGTH: 76
<212> TYPE: DNA
<213> ORGANISM: artificial sequence
<220> FEATURE:
<223> OTHER INFORMATION: synthesized

<400> SEQUENCE: 45
tggtgcctct gactggactc gaaccagtga catacggatt tagagtccgc cgttctaccg    60
actgaactac agaggc    76

<210> SEQ ID NO 46
<211> LENGTH: 77
<212> TYPE: RNA
<213> ORGANISM: artificial sequence
<220> FEATURE:
<223> OTHER INFORMATION: synthesized

<400> SEQUENCE: 46
ggaucgaaag auuuccgcag gcccgaaagg guauuggcgu uaggugcggg augcuacaaa    60
aaaaaaaaaa aaaaaaa    77

<210> SEQ ID NO 47
<211> LENGTH: 35
<212> TYPE: DNA
<213> ORGANISM: artificial sequence
<220> FEATURE:
<223> OTHER INFORMATION: synthesized

<400> SEQUENCE: 47
catatggcta gcaaaggaga agaactttc actgg    35

<210> SEQ ID NO 48
<211> LENGTH: 51
<212> TYPE: DNA
<213> ORGANISM: artificial sequence
<220> FEATURE:
<223> OTHER INFORMATION: synthesized

<400> SEQUENCE: 48
atactcaagc ttagtggtgg tggtggtggt gtttgtagag ctcatccatg c    51

<210> SEQ ID NO 49
<211> LENGTH: 35
<212> TYPE: RNA
<213> ORGANISM: artificial sequence
<220> FEATURE:
<223> OTHER INFORMATION: synthesized

<400> SEQUENCE: 49
ggugguacga gauucgaauc cucguaccgc agcca    35

<210> SEQ ID NO 50
<211> LENGTH: 4
<212> TYPE: DNA
<213> ORGANISM: artificial sequence
<220> FEATURE:
<223> OTHER INFORMATION: synthesized

<400> SEQUENCE: 50 gggt    4

<210> SEQ ID NO 51
<211> LENGTH: 15
<212> TYPE: RNA
<213> ORGANISM: artificial sequence
<220> FEATURE:
<223> OTHER INFORMATION: synthesized

<400> SEQUENCE: 51

-continued

```
aauguauaga ucacg                                                    15

<210> SEQ ID NO 52
<211> LENGTH: 5
<212> TYPE: PRT
<213> ORGANISM: artificial sequence
<220> FEATURE:
<221> NAME/KEY: unsure
<222> LOCATION: 3
<223> OTHER INFORMATION: synthesized; Xaa is any natural or modified
      amino acid

<400> SEQUENCE: 52

Asn Val Xaa Ile Thr
  1               5

<210> SEQ ID NO 53
<211> LENGTH: 15
<212> TYPE: RNA
<213> ORGANISM: artificial  sequence
<220> FEATURE:
<223> OTHER INFORMATION: synthesized

<400> SEQUENCE: 53
aauguauaca ucacg                                                    15

<210> SEQ ID NO 54
<211> LENGTH: 5
<212> TYPE: PRT
<213> ORGANISM: artificial sequence
<220> FEATURE:
<223> OTHER INFORMATION: synthesized

<400> SEQUENCE: 54

Asn Val Tyr Ile Thr
  1               5

<210> SEQ ID NO 55
<211> LENGTH: 16
<212> TYPE: RNA
<213> ORGANISM: artificial sequence
<220> FEATURE:
<223> OTHER INFORMATION: synthesized

<400> SEQUENCE: 55
guucaagggu gcugac                                                   16

<210> SEQ ID NO 56
<211> LENGTH: 5
<212> TYPE: PRT
<213> ORGANISM: artificial sequence
<220> FEATURE:
<221> NAME/KEY: unsure
<222> LOCATION: 3
<223> OTHER INFORMATION: synthesized; Xaa can be any natural or non-
      natural amino acid

<400> SEQUENCE: 56

Val Gln Xaa Ala Asp
  1               5

<210> SEQ ID NO 57
<211> LENGTH: 4
<212> TYPE: Prt
<213> ORGANISM: artificial sequence
<220> FEATURE:
<223> OTHER INFORMATION: synthesized
```

```
<400> SEQUENCE: 57

Val Gln Gly Cys
 1           4

<210> SEQ ID NO 58
<211> LENGTH: 15
<212> TYPE: RNA
<213> ORGANISM: artificial sequence
<220> FEATURE:
<223> OTHER INFORMATION: synthesized

<400> SEQUENCE: 58
guucaacuag cugac                                                  15

<210> SEQ ID NO 59
<211> LENGTH: 5
<212> TYPE: PRT
<213> ORGANISM: artificial sequence
<220> FEATURE:
<223> OTHER INFORMATION: synthesized

<400> SEQUENCE: 59

Val Gln Leu Ala Asp
 1               5

<210> SEQ ID NO 60
<211> LENGTH: 77
<212> TYPE: DNA
<213> ORGANISM: artificial sequence
<220> FEATURE:
<223> OTHER INFORMATION: synthesized

<400> SEQUENCE: 60
tggtgcctct gactggactc gaaccagtga catacggatt gggtagtccg ccgttctacc    60
gactgaacta cagaggc                                                   77

<210> SEQ ID NO 61
<211> LENGTH: 4
<212> TYPE: RNA
<213> ORGANISM: artificial sequence
<220> FEATURE:
<223> OTHER INFORMATION: synthesized

<400> SEQUENCE: 61 ggcg                                                               4
```